United States Patent
Miyano et al.

(10) Patent No.: US 12,414,945 B2
(45) Date of Patent: Sep. 16, 2025

(54) THERAPEUTIC AGENT FOR BREAST CANCER

(71) Applicant: Eisai R&D Management Co., Ltd., Tokyo (JP)

(72) Inventors: Saori Miyano, Tsukuba (JP); Yuji Yamamoto, Tsukuba (JP); Takayuki Nakagawa, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 15/771,193

(22) PCT Filed: Dec. 15, 2016

(86) PCT No.: PCT/JP2016/087349
§ 371 (c)(1),
(2) Date: Apr. 26, 2018

(87) PCT Pub. No.: WO2017/104739
PCT Pub. Date: Jun. 22, 2017

(65) Prior Publication Data
US 2018/0303817 A1    Oct. 25, 2018

(30) Foreign Application Priority Data
Dec. 17, 2015  (JP) .................... 2015-246308

(51) Int. Cl.
A61K 31/445    (2006.01)
A61K 31/4545   (2006.01)
A61P 35/04     (2006.01)

(52) U.S. Cl.
CPC .......... *A61K 31/4545* (2013.01); *A61P 35/04* (2018.01)

(58) Field of Classification Search
CPC ..................... A61K 31/4545; A61P 35/04
See application file for complete search history.

(56) References Cited

U.S. PATENT DOCUMENTS

| | | |
|---|---|---|
| 6,831,175 B2 | 12/2004 | Li et al. |
| 7,109,219 B2 | 9/2006 | Tsuruoka et al. |
| 7,253,286 B2 | 8/2007 | Funahashi et al. |
| 8,131,527 B1 | 3/2012 | Saxty et al. |
| 8,614,216 B2 | 12/2013 | Okhamafe et al. |
| 8,933,099 B2 | 1/2015 | Funahashi et al. |
| 9,951,047 B2 | 4/2018 | Ozaki et al. |
| 2004/0053908 A1 | 3/2004 | Funahashi et al. |
| 2004/0122029 A1 | 6/2004 | Liu et al. |
| 2004/0204427 A1 | 10/2004 | Chen et al. |
| 2005/0187236 A1 | 8/2005 | Tsuruoka et al. |
| 2005/0256154 A1 | 11/2005 | Luk et al. |
| 2008/0108648 A1 | 5/2008 | Alcouffe et al. |
| 2011/0060215 A1 | 3/2011 | Tupin et al. |
| 2012/0270918 A1 | 10/2012 | Abecassis et al. |
| 2013/0338134 A1 | 12/2013 | Wu et al. |
| 2014/0142084 A1 | 5/2014 | Kameda et al. |
| 2014/0155385 A1 | 6/2014 | Barf et al. |
| 2014/0235614 A1 | 8/2014 | Funasaka et al. |
| 2014/0378422 A1 | 12/2014 | Yovine et al. |
| 2015/0191791 A1 | 7/2015 | Shibata |
| 2017/0217935 A1 | 8/2017 | Ozaki et al. |
| 2018/0065951 A1 | 3/2018 | Buschmann et al. |
| 2018/0303817 A1 | 10/2018 | Miyano et al. |
| 2020/0277387 A1 | 9/2020 | Currie |
| 2020/0375970 A1 | 12/2020 | Yamaguchi et al. |
| 2023/0149381 A1 | 5/2023 | Nishibata et al. |

FOREIGN PATENT DOCUMENTS

| | | |
|---|---|---|
| AU | 2014219811 | 8/2014 |
| CA | 2974937 | 9/2016 |
| CA | 3001969 | 6/2017 |
| CA | 3091153 | 10/2019 |
| CL | 201400130 | 8/2014 |
| CN | 1678607 | 10/2005 |
| CN | 101024627 | 8/2007 |
| CN | 103917545 | 7/2014 |
| CN | 106660997 | 5/2017 |
| CN | 107205996 | 9/2017 |
| EP | 1415987 | 5/2004 |
| EP | 1522540 | 4/2005 |
| EP | 2657233 | 8/2014 |
| JP | 2008-533111 | 3/2006 |
| JP | 2006-522756 | 10/2006 |
| JP | 2009-108032 | 5/2009 |
| JP | 2009-215313 | 9/2009 |
| JP | 5600229 | 10/2014 |
| JP | 2014-237707 | 12/2014 |
| JP | 2015-505562 | 2/2015 |
| JP | 5925978 | 4/2016 |
| JP | 2017-206437 | 11/2017 |
| JP | 2018-507220 | 3/2018 |
| JP | 2018-512391 | 5/2018 |

(Continued)

OTHER PUBLICATIONS

Gould (International Journal of Pharmaceutics. 33 (1986), pp. 201-217.*
European Search Report in European Application No. 16768810.0, dated Dec. 11, 2018, 7 pages.
Notice of Allowance in Mexican Patent Application No. MX/a/2015/010698, dated Nov. 8, 2018, 4 pages (English Translation).
Notice of Allowance in Taiwanese Application No. 103105419, dated Sep. 11, 2018, 5 pages (English Translation).
Notice of Allowance in U.S. Appl. No. 15/547,139, dated Sep. 28, 2018, 16 pages.
Office Action in Israeli Patent Application No. 253701, dated Oct. 17, 2018, 7 pages (with English Translation).

(Continued)

*Primary Examiner* — Shobha Kantamneni
(74) *Attorney, Agent, or Firm* — Fish & Richardson P.C.

(57) ABSTRACT

The present application discloses a therapeutic agent for breast cancer, comprising 5-((2-(4-(1-(2-hydroxyethyl)piperidin-4-yl)benzamide)pyridin-4-yl)oxy)-6-(2-methoxyethoxy)-N-methyl-1H-indole-1-carboxamide or a pharmacologically acceptable salt thereof.

4 Claims, 2 Drawing Sheets

(56) References Cited

FOREIGN PATENT DOCUMENTS

| | | |
|---|---|---|
| JP | 2018-538274 | 12/2018 |
| KR | 10-2005-0059151 | 6/2005 |
| KR | 10-2017-0035927 | 3/2017 |
| KR | 102050128 | 11/2019 |
| RU | 2257380 | 7/2005 |
| RU | 2005108999 | 8/2005 |
| RU | 2345077 | 2/2006 |
| RU | 2310651 | 11/2007 |
| TW | 200413353 | 8/2004 |
| WO | WO 2002/032872 | 4/2002 |
| WO | WO 2004/002410 | 1/2004 |
| WO | WO 2004/020434 | 3/2004 |
| WO | WO 2006/000420 | 1/2006 |
| WO | WO 2006/097625 | 9/2006 |
| WO | WO 2007/071752 | 6/2007 |
| WO | WO 2008/008747 | 1/2008 |
| WO | WO 2008/012690 | 1/2008 |
| WO | WO 2008/075068 | 6/2008 |
| WO | WO 2008/078091 | 7/2008 |
| WO | WO 2008/078100 | 7/2008 |
| WO | WO 2009/001070 | 12/2008 |
| WO | WO 2009/019518 | 2/2009 |
| WO | WO 2009/047506 | 4/2009 |
| WO | WO 2009/047522 | 4/2009 |
| WO | WO 2009/056886 | 5/2009 |
| WO | WO 2009/076602 | 6/2009 |
| WO | WO 2009/117421 | 9/2009 |
| WO | WO 2009/141386 | 11/2009 |
| WO | WO 2009/150240 | 12/2009 |
| WO | WO 2009/153592 | 12/2009 |
| WO | WO 2010/078421 | 7/2010 |
| WO | WO 2010/078427 | 7/2010 |
| WO | WO 2010/078430 | 7/2010 |
| WO | WO 2010/119284 | 10/2010 |
| WO | WO 2010/119285 | 10/2010 |
| WO | WO 2011/001122 | 1/2011 |
| WO | WO 2011/001413 | 1/2011 |
| WO | WO 2011/016528 | 2/2011 |
| WO | WO 2011/051425 | 5/2011 |
| WO | WO 2011/071821 | 6/2011 |
| WO | WO 2011/135376 | 11/2011 |
| WO | WO 2012/004732 | 1/2012 |
| WO | WO 2012/073017 | 6/2012 |
| WO | WO 2012/088266 | 6/2012 |
| WO | WO 2013/010380 | 1/2013 |
| WO | WO 2013/061074 | 5/2013 |
| WO | WO 2013/061077 | 5/2013 |
| WO | WO 2013/061080 | 5/2013 |
| WO | WO 2013/061081 | 5/2013 |
| WO | WO 2013/087744 | 6/2013 |
| WO | WO 2013/108809 | 7/2013 |
| WO | WO 2013/116293 | 8/2013 |
| WO | WO 2013/129369 | 9/2013 |
| WO | WO 2013/151913 | 10/2013 |
| WO | WO 2013/179034 | 12/2013 |
| WO | WO 2014/007369 | 1/2014 |
| WO | WO 2014/011900 | 1/2014 |
| WO | WO 2014/026125 | 2/2014 |
| WO | WO 2014/044846 | 3/2014 |
| WO | WO 2014/048878 | 3/2014 |
| WO | WO 2014/051022 | 3/2014 |
| WO | WO 2014/129477 | 8/2014 |
| WO | WO 2014/145751 | 9/2014 |
| WO | WO 2014/162039 | 10/2014 |
| WO | WO 2016/027781 | 2/2016 |
| WO | WO 2016/084883 | 6/2016 |
| WO | WO 2016/134234 | 8/2016 |
| WO | WO 2016/141218 | 9/2016 |
| WO | WO 2016/152907 | 9/2016 |
| WO | WO 2017/091577 | 6/2017 |
| WO | WO 2017/104739 | 6/2017 |
| WO | WO 2018/049233 | 3/2018 |
| WO | WO 2019/189241 | 10/2019 |
| WO | WO 2020/014440 | 1/2020 |
| WO | WO 2021/210636 | 10/2021 |

OTHER PUBLICATIONS

Office Action in Israeli Patent Application No. 250290, dated Sep. 2, 2018, 5 pages (English Translation).
Submission Document in Chinese Patent Application No. 201580042132.3, dated Oct. 22, 2018, 15 pages (with English Translation).
Submission Document in Chinese Patent Application No. 201680068110.9, dated Oct. 8, 2018, 11 pages (with English Translation).
Submission Document in European Patent Application No. 15834302.0, dated Oct. 2, 2018, 80 pages.
Submission Document in U.S. Appl. No. 15/547,139, dated Dec. 17, 2018.
Notice of Allowance in Chinese Patent Application No. 201580042132.3, dated Mar. 6, 2019, 4 pages (with English Translation).
Notice of Allowance in New Zealand Patent Application No. 711101, dated Jul. 27, 2018, 1 page.
Notice of Allowance in U.S. Appl. No. 15/547,139, dated Mar. 6, 2019, 13 pages.
Office Action in New Zealand Patent Application No. 711101, dated May 1, 2018, 2 pages.
Submission Document in Australian Patent Application No. 2015304465, dated Apr. 5, 2019, 16 pages.
Submission Document in Canadian Patent Application No. 2901585, dated Mar. 25, 2019, 42 pages.
Submission Document in Indian Patent Application No. 4989/CHENP/2015, dated Apr. 15, 2019, 24 pages.
Submission Document in Israeli Patent Application No. 250290, dated Dec. 26, 2018, 4 pages.
Submission Document in U.S. Appl. No. 16/225,772, dated Dec. 19, 2018, 104 pages.
"Cancer classification, NCI, from internet", 2008, p. 1-p. 3.
Andre et al., " Targeting FGFR with Dovitinib (TKI258): Preclinical and Clinical Data in Breast Cancer", Clinical Cancer Research, vol. 19, No. 13, Jul. 1, 2013, p. 3693-p. 3702.
Applicant's unpublished experimental data, 2014, 1 page.
Arai et. al, "Fibroblast Growth Factor Receptor 2 Tyrosine Kinase Fusions Define a Unique Molecular Subtype of Cholangiocarcinoma", Hepatology, 2014, vol. 59, No. 4, p. 1427-p. 1434.
Berrada et al., "Treatment of triple-negative metastatic breast cancer: toward individualized targeted treatments or chemosensitization?," Annals of Oncology, vol. 21, Supplement 7, 2010, p. vii30-p. vii35.
Bono et al., "Inhibition of Tumor Angiogenesis and Growth by a Small-Molecule Multi-FGF Receptor Blocker with Allosteric Properties", Cancer Cell, 2013, p. 477-p. 488.
Borad et al., "Integrated Genomic Characterization Reveals Novel, Therapeutically Relevant Drug Targets in FGFR and EGFR Pathways in Sporadic Intrahepatic Cholangiocarcinoma", PLOS GENETICS, 2014, vol. 10, Issue 2, p. 1-p. 21.
Bucci et al., "Circadian Rhythms: channels contribute," Nature Chem Bio., Jun. 2013, 9:349.
Cancer Genome Atlas Research Network, "Comprehensive genomic characterization of squamous cell lung cancers," Nature, 2012, 489(7417):519-525.
Celina Ang, "Role of the fibroblast growth factor receptor axis in cholangiocarcinoma", Journal of Gastroenterology and Hepatology, 2015, vol. 30, p. 1116-p. 1122.
Chen et al., "Inhibition of endogenous SPARC enhances pancreatic-cancer cell growth: modulation by FGFR1-III isoform expression", Br J Cancer, 2010(102), p. 188-p. 195.
Daniele et al., "FGF Receptor Inhibitors: Role in Cancer Therapy", Curr Oncol Rep., 2012(14), p. 111-p. 119.
Dey et al., "Targeting Fibroblast Growth Factor Receptors Blocks PI3K/AKT Signaling, Induces Apoptosis, and Impairs Mammary Tumor Outgrowth and Metastasis," Cancer Research, vol. 70, No. 10, May 15, 2010, p. 4151-p. 4162.

(56) References Cited

OTHER PUBLICATIONS

European Search Report in European Application No. 14754294.8, dated Jul. 15, 2016, 5 pages.
European Search Report in European Application No. 15834302.0, dated Mar. 15, 2018, 6 pages.
European Search Report in European Application No. 16768810.0, dated Aug. 17, 2018, 7 pages.
Foulkes et al., "Triple-Negative Breast Cancer," The New England Journal of Medicine, Nov. 11, 2010, 363:1938-1948.
French et al., "Targeting FGFR4 Inhibits Hepatocellular Carcinoma in Preclinical Mouse Models", PLoS One, 2012(7), p. 1-p. 12.
Gavine et al., "AZD4547:An Orally Bioavailable, Potent, and Selective Inhibitor of the Fibroblast Growth Factor Receptor Tyrosine Kinase Family", Cancer Res, 2012(72), p. 2045-p. 2056.
Guagnano et al., "Discovery of 3-(2,6-Dichloro-3,5-dimethoxyphenyl)-1-{6-[4-(4-ethyl-piperazin-l-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase", J Med Chem, 2011(54).
Guagnano et al., "FGFR Genetic Alterations Predict for Sensitivity to NVP-BGJ398, a Selective Pan-FGFR Inhibitor", Cancer Discovery, Sep. 20, 2012, p. 1118-p. 1133.
Harbinski et al., "Rescue Screens with Secreted Proteins Reveal Compensatory Potential of Receptor Tyrosine Kinases in Driving Cancer Growth", Cancer Discovery, Aug. 8, 2012 p. 948-p. 958.
International Preliminary Report on Patentability in International Application No. PCT/JP2014/053819, dated Sep. 3, 2015, 7 pages.
International Preliminary Report on Patentability in International Application No. PCT/JP2015/073047, dated Mar. 2, 2017, 6 pages (English Translation).
International Preliminary Report on Patentability in Patent Application No. PCT/JP2016/059162, dated Oct. 5, 2017, 8 pages (English Translation).
International Preliminary Report on Patentability in Patent Application No. PCT/JP2016/087349, dated Jun. 28, 2018, 9 pages.
International Search Report for PCT/JP2015/073047 dated Nov. 17, 2015 (English translation).
International Search Report in International Application No. PCT/JP2014/053819, dated Apr. 15, 2014, 9 pages.
International Search Report in International Application No. PCT/JP2016/059162, dated May 24, 2016, 2 pages (English Translation).
International Search Report in International Application No. PCT/JP2016/087349, dated Feb. 7, 2017, 2 pages (English Translation).
Ishiwata et al., "Enhanced Expression of Fibroblast Growth Factor Receptor 2 IIIc Promotes Human Pancreatic Cancer Cell Proliferation", Am J Pathol, 2012(180), p. 1928-p. 1941.
Koziczak et al., "Blocking of FGFR signaling inhibits breast cancer cell proliferation through downregulation of D-type cyclins", Oncogene, vol. 23, 2004, p. 3501-p. 3508.
Li et al., "Preparation of heteroaryls for therapeutic use in pharmaceutical compositions as kinase inhibitors for treatment of hyperproliferative diseases, including cancer," 2003, CA139:323437.
Logie et al., "Activating mutations of the tyrosine kinase receptor FGFR3 are associated with benign skin tumors in mice and humans", Hum Mol Genet, 2005(14), p. 1153-p. 1160.
Mohammadi et al., "Crystal structure of an angiogenesis inhibitor bound to the FGF receptor .tyrosine kinase domain", The EMBO Journal vol. 17 No. 20, 1998, p. 5896-p. 5904.
Nicholas et al., "Fibroblast growth factor signalling: from development to cancer", Nature Reviews Cancer, 2010(10), p. 116-p. 129.
Norman et al., "Protein-Ligand Crystal Structures Can Guide the Design of Selective Inhibitors of the FGFR Tyrosine Kinase", Journal of Medicinal Chemistry, May 21, 2012, p. 5003-p. 5012.
Notice of Allowance in Australian Patent Application No. 2014219811, dated Sep. 13, 2017, 3 pages.
Notice of Allowance in Chinese Patent Application No. 201480009370.X dated Jul. 25, 2017, 4 pages (English Translation).
Notice of Allowance in European Patent Application No. 14754294.8, dated Jan. 4, 2017, 239 pages.
Notice of Allowance in European Patent Application No. 14754294.8, dated Mar. 9, 2017, 2 pages.
Notice of Allowance in Gulf Cooperation Council Patent Application GCC/P/2014/26467, dated Jan. 7, 2018, 2 pages (English Translation).
Notice of Allowance in Japanese Patent Application No. P2015-560425, dated Apr. 19, 2016, 6 pages (English Translation).
Notice of Allowance in Russian Patent Application No. 2015134558, dated Jan. 10, 2018, 25 pages (English Translation).
Notice of Allowance in Russian Patent Application No. 2017103439, dated Apr. 10, 2018, 14 pages (English Translation).
Notice of Allowance in Singaporean Patent Application No. 11201506488W, dated Sep. 20, 2017 (English Translation).
Notice of Allowance in Singaporean Patent Application No. 11201700703X, dated Sep. 12, 2017, 5 pages (English Translation).
Notice of Allowance in South African Application No. 2015/05941, dated May 24, 2016, 6 pages.
Notice of Allowance in U.S. Appl. No. 15/500,429, dated Jan. 18, 2018, 6 pages.
Notice of Allowance in U.S. Appl. No. 15/500,429, dated Mar. 29, 2018, 4 pages.
Notice of Allowance in U.S. Appl. No. 14/183,864, dated Nov. 19, 2014, 11 pages.
Notice of Allowance in U.S. Appl. No. 15/500,429, dated Oct. 19, 2017, 11 pages.
Notice of Allowance in Ukrainian Patent Application a201508149, dated Jan. 3, 2018, 16 pages (English Translation).
Notice of Allowance in Vietnamese Patent Application No. 1-2015-02994, dated Oct. 23, 2017, 2 pages (English Translation).
Office Action in Australian Patent Application No. 2014219811, dated Jun. 16, 2017, 2 pages.
Office Action in Chilean Patent Application No. 2015-02311, dated Mar. 22, 2017, 21 pages (English Translation).
Office Action in Chilean Patent Application No. 2015-02311, dated Sep. 13, 2017, 13 pages (English Translation).
Office Action in Chinese Application No. 201480009370.X, dated Jan. 9, 2017, 10 pages (English Translation).
Office Action in Chinese Application No. 201480009370.X, dated May 26, 2016, 7 pages (English Translation).
Office Action in Chinese Patent Application No. 201580042132.3, dated Aug. 8, 2018, 11 pages (English Translation).
Office Action in Gulf Cooperation Council Patent Application No. GCC/P/2014/26467, dated Jun. 7, 2017, 7 pages (English Translation).
Office Action in Israeli Application No. 240623, dated Jan. 19, 2016, 5 pages (English Translation).
Office Action in Israeli Patent Application No. 240623, dated Dec. 20, 2017, 8 pages (English Translation).
Office Action in Japanese Application No. P2015-560425, dated Mar. 8, 2016, 4 pages (English Translation).
Office Action in Mexican Patent Application No. MX/a/2015/010698, dated Jun. 15, 2018, 9 pages (English Translation).
Office Action in Pakistani Patent Application No. 523/2016, dated May 3, 2018, 2 pages (English Translation).
Office Action in Pakistani Patent Application No. 94/2014, dated May 3, 2018, 2 pages (English Translation).
Office Action in Pakistani Patent Application No. 94/2014, dated May 13, 2016, 2 pages.
Office Action in Russian Patent Application No. 2015134558, dated Aug. 24, 2017, 11 pages (English Translation).
Office Action in Russian Patent Application No. 2015134558, dated Oct. 21, 2015, 3 pages (English Translation).
Office Action in Russian Patent Application No. 2017103439, dated Feb. 6, 2018, 6 pages (English Translation).
Office Action in Singaporean Patent Application No. 11201700703X, dated Jun. 8, 2017, 5 pages (English Translation).
Office Action in Taiwanese Patent Application No. 103105419, dated May 14, 2018, 4 pages (English Translation).
Office Action in Taiwanese Patent Application No. 103105419, dated Oct. 24, 2017, 7 pages (English Translation).
Office Action in Thai Patent Application No. 1501004679, dated Jun. 11, 2018, 4 pages (English Translation).

(56) References Cited

OTHER PUBLICATIONS

Office Action in Thai Patent Application No. 1501004679, dated Sep. 26, 2017, 4 pages (English Translation).
Office Action in Ukrainian Patent Application No. a201508149, dated Aug. 11, 2017, 6 pages (English Translation).
Office Action in Ukrainian Patent Application No. a201508149, dated Oct. 6, 2015, 2 pages (English Translation).
Office Action in U.S. Appl. No. 14/183,864, dated Jun. 4, 2014, 7 pages.
Office Action in U.S. Appl. No. 14/183,864, dated Sep. 16, 2014.
Office Action in U.S. Appl. No. 15/500,429, dated Jul. 31, 2017, 8 pages.
Office Action in U.S. Appl. No. 15/547,139, dated Apr. 30, 2018, 26 pages.
Office Action in Vietnamese Patent Application No. 1-2015-02994, dated Jun. 21, 2017, 2 pages (English Translation).
Office Action in Vietnamese Patent Application No. 1-2015-02994, dated Sep. 30, 2015, 4 pages (English Translation).
Patani and LaVoie, "Bioisosterism: A Rational Approach in Drug Design," Chem. Rev., 1996, 96:3147-3176.
Request to Amend Application Before Grant in Singapore Patent Application No. 11201506488W, dated Aug. 3, 2017, 21 pages (English Translation).
Response in Gulf Cooperation Council Patent Application No. GCC/P/2014/26467, dated Aug. 27, 2017, 18 pages (English Translation).
Response in Malaysian Patent Application No. PI2015702696, dated Nov. 6, 2017, 8 pages (English Translation).
Response in U.S. Appl. No. 15/500,429, dated Sep. 27, 2017, 6 pages.
Response in Vietnamese Patent Application No. 1-2015-02994, dated Aug. 7, 2017, 2 pages (English Translation).
Rubini et al., "Synthesis of Isosteric Methylene-Oxy Pseudodipeptide Analogues as Novel Amide Bond Surrogate Units", Tetrahedron, vol. 42, No. 21, 1986, p. 6039-p. 6045.
Sasaki et al., "Increased FGFR1 copy number in lung squamous cell carcinomas", Mol Med Report, 2012(5), p. 725-p. 728.
Shibata, "Clinical significance of Expression oFGFR2 Fusion Genes in Bile Duct Cancer", The Bilialy Tract & Pancreas, Feb. 12, 2015, vol. 36(2), p. 137-p. 142.
St. Bernard et al., "Fibroblast Growth Factor Receptors as Molecular Targets in Thyroid Carcinoma", Endocrinology, 2005(146), p. 1145-p. 1153.
Submission Document in Argentine Patent Application No. P140100495, dated Jan. 23, 2015, 7 pages (English Translation).
Submission Document in Australian Patent Application No. 2014219811, dated Aug. 22, 2017, 6 pages.
Submission Document in Brazilian Patent Application No. BR112015019790-6, dated Apr. 28, 2016, 19 pages (English Translation).
Submission Document in Brazilian Patent Application No. BR112015019790-6, dated Dec. 22, 2015, 12 pages (English Translation).
Submission Document in Chilean Patent Application No. 2015-02311, dated Dec. 18, 2017, 40 pages (English Translation).
Submission Document in Chilean Patent Application No. 2015-02311, dated Jan. 8, 2016, 8 pages.
Submission Document in Chilean Patent Application No. 2015-02311, dated Jun. 13, 2017, 38 pages (English Translation).
Submission Document in Chinese Patent Application No. 201480009370.X, dated Feb. 25, 2016, 18 pages (English Translation).
Submission Document in Chinese Patent Application No. 201480009370.X, dated Mar. 21, 2017, 41 pages (English Translation).
Submission Document in Chinese Patent Application No. 201480009370.X, dated Oct. 10, 2016, 59 pages (English Translation).
Submission Document in Egyptian Patent Application No. PCT1285/2015, dated Aug. 19, 2015, 2 pages (English Translation).
Submission Document in European Patent Application No. 14754294.8, dated Nov. 10, 2016, 9 pages.
Submission Document in Indian Patent Application No. 4989/CHENP/2015, dated May 9, 2016, 7 pages (English Translation).
Submission Document in Indonesian Patent Application No. P-00201505035, dated Apr. 27, 2016, 10 pages (English Translation).
Submission Document in Indonesian Patent Application No. P-00201505035, dated Dec. 5, 2016, 3 pages.
Submission Document in Israeli Patent Application No. 240623, dated May 18, 2016, 3 pages (English Translation).
Submission Document in Japanese Patent Application No. 2014-526292, dated May 30, 2014, 14 pages (English Translation).
Submission Document in Japanese Patent Application No. P2015-560425, dated Mar. 24, 2016, 8 pages (English Translation).
Submission Document in Jordanian Patent Application No. 39/2014, dated Mar. 15, 2018, 12 pages (English Translation).
Submission Document in Malaysian Patent Application No. PI 2015702696, dated Apr. 7, 2016, 4 pages.
Submission Document in Malaysian Patent Application No. PI 2015702696, dated Jan. 6, 2016, 207 pages.
Submission Document in Mexican Patent Application No. MX/a/2015/010698, dated Aug. 2, 2018, 17 pages (English Translation).
Submission Document in New Zealand Patent Application No. 711101, dated Apr. 12, 2016, 9 pages.
Submission Document in New Zealand Patent Application No. 711101, dated Jan. 20, 2016, 5 pages.
Submission Document in New Zealand Patent Application No. 711101, dated Jul. 20, 2018, 6 pages.
Submission Document in Pakistani Patent Application No. 523/2016, dated Jun. 4, 2018, 1 page (English Translation).
Submission Document in Pakistani Patent Application No. 94/2014, dated Aug. 25, 2016, 14 pages.
Submission Document in Pakistani Patent Application No. 94/2014, dated Jul. 7, 2018, 4 pages.
Submission Document in Peruvian Patent Application No. 001748-2015, dated Dec. 21, 2015, 9 pages (English Translation).
Submission Document in Philippine Patent Application No. 1-2015-501813, dated Apr. 4, 2016, 1 page (English Translation).
Submission Document in Philippine Patent Application No. 1-2015-501813, dated Dec. 21, 2015, 3 pages (English Translation).
Submission Document in Russian Patent Application No. 2015134558, dated Apr. 22, 2016, 14 pages (English Translation).
Submission Document in Russian Patent Application No. 2015134558, dated Dec. 25, 2015, 16 pages.
Submission Document in Russian Patent Application No. 2015134558, dated Nov. 22, 2017, 21 pages (English Translation).
Submission Document in Russian Patent Application No. 2017103439, dated Mar. 20, 2018, 19 pages (English Translation).
Submission Document in Singaporean Patent Application No. 11201506488W, dated Dec. 23, 2015, 5 pages.
Submission Document in Singaporean Patent Application No. 11201700703X, dated Jul. 19, 2017, 16 pages (English Translation).
Submission Document in Taiwanese Patent Application No. 103105419, dated Aug. 8, 2018, 19 pages (English Translation).
Submission Document in Taiwanese Patent Application No. 103105419, dated Jan. 23, 2018, 30 pages (English Translation).
Submission Document in Thai Patent Application No. 1501004679, dated Jul. 20, 2018, 4 pages (English Translation).
Submission Document in Thai Patent Application No. 1501004679, dated Nov. 20, 2017, 6 pages (English Translation).
Submission Document in Ukrainian Patent Application No. a201508149, dated Nov. 20, 2017, 20 pages (English Translation).
Submission Document in Ukrainian Patent Application No. a201508149, dated Oct. 6, 2015, 4 pages (English Translation).
Submission Document in U.S. Appl. No. 15/547,139, dated Jul. 25, 2018, 13 pages.
Submission Document in Vietnamese Patent Application No. 1-2015-02994, dated May 25, 2016, 12 pages (English Translation).
Submission Document in Vietnamese Patent Application No. 1-2015-02994, dated Oct. 28, 2015, 22 pages (English Translation).

(56) References Cited

OTHER PUBLICATIONS

Tsimafeyeu et al., "Overexpression of fibroblast growth factor receptors FGFR1 and FGFR2 in renal cell carcinoma", Scand J Urol Nephrol, 2011(45), p. 190-p. 195.
Turner et al., "FGFRI Amplification Drives Endocrine Therapy Resistance and is a Therapeutic Target in Breast Cancer," Cancer Research, vol. 70, No. 5, Mar. 1, 2010, p. 2085-p. 2094.
Turner et al., "Fibroblast growth factor signaling: from development to cancer", Nature Reviews Cancer, 2010 vol. 10, p. 116-p. 129.
Watanabe Miyano et al., "E7090, a Novel Selective Inhibitor of Fibroblast Growth Factor Receptors, Displays Potent Antitumor Activity and Prolongs Survival in Preclinical Models," Molecular Cancer Therapeutics, vol. 15, No. 11, Nov. 2016, p. 2630-p. 2639.
Weiss et al., "Frequent and Focal FGFR1 Amplification Associates with Therapeutically Tractable FGFR1 Dependency in Squamous Cell Lung Cancer", Sci Transl Med, Apr. 18, 2012, p. 1-p. 7.
Wesche et al., "Fibroblast growth factors and their receptors in cancer", Biochem J., 2011(437), p. 199-p. 213.
Zhang et al., "Translating the Therapeutic Potential of AZD4547 in FGFR1-Amplified Non-Small Cell Lung Cancer through the Use of Patient-Derived Tumor Xenograft Models", Clinical Cancer Research, May 24, 2013, p. 6657-p. 6667.
Office Action in Australian Patent Application No. 2015304465, dated Jan. 21, 2019, 2 pages.
Office Action in Canadian Patent Application No. 2901585, dated Jan. 30, 2019, 3 pages.
Office Action in Israeli Patent Application No. 240623, dated Jan. 7, 2019, 7 pages (English Translation).
Submission Document in European Patent Application No. 16768810.0, dated Feb. 11, 2019, 9 pages.
Submission Document in Israeli Patent Application No. 253701, dated Feb. 4, 2019, 8 pages (English Translation).
Notice of Allowance in Japanese Patent Application No. P2017-508383, dated Mar. 5, 2019, 6 pages (with English Translation).
Office Action in Indian Patent Application No. 4989/CHENP/2015, dated Jan. 31, 2019, 5 pages.
Office Action in Indonesian Patent Application No. P-00201505035, dated Feb. 1, 2019, 5 pages, (with English Translation).
Submission Document in Brazilian Patent Application No. BR1120170163926, dated Mar. 6, 2019, 16 pages (with English Translation).
Submission Document in Japanese Patent Application No. P2017-508383, dated Feb. 8, 2019, 80 pages.
Office Action in Israeli Patent Application No. 258671, dated Aug. 4, 2019, 5 page (with English Translation).
Notice of Allowance in Taiwanese Application No. 107134526, dated Jul. 29, 2019, 7 pages (with English Translation).
Submission Document in Singaporean Patent Application No. 11201706143S, dated May 30, 2019, 13 pages.
Submission Document in U.S. Appl. No. 15/547,139, dated Apr. 30, 2019, 11 pages.
European Search Report in European Application No. 16875716.9, dated Jul. 29, 2019, 9 pages.
Notice of Allowance in Canadian Patent Application No. 2901585, dated Jun. 5, 2019, 1 page (with English Translation).
Notice of Allowance in Taiwanese Application No. 107134522, dated Jul. 29, 2019, 7 pages (with English Translation).
Notice of Allowance in Taiwanese Application No. 107134529, dated Jul. 29, 2019, 7 pages (with English Translation).
Office Action in Chinese Patent Application No. 201680007472.7, dated Jun. 14, 2019, 14 pages (with English Translation).
Office Action in U.S. Appl. No. 16/225,722, dated Jul. 9, 2019, 33 pages.
Submission Document in Peruvian Patent Application No. 001748-2015, dated Jul. 6, 2019, 6 pages (with English Translation).
Submission Document in Peruvian Patent Application No. 001748-2015, dated Jun. 21, 2019, 4 pages (with English Translation).
Watanabe et al., "Abstract 770: E7090: A potent and selective FGFR inhibitor with activity in multiple FGFR-driven cancer models with distinct mechanisms of activation," Cancer Research, 2015, 75(Suppl. 15):1-4, XP002792860 (Abstract Only).
Office Action in Russian Patent Application No. 2017127135, dated Aug. 22, 2019, 16 pages (with English Translation).
Office Action in Indian Patent Application No. 201747003469, dated Aug. 2, 2019, 5 pages (with English Translation).
Office Action in Mexican Patent Application No. MX/a/2017/001624, dated Jun. 25, 2019, 8 pages (with English Translation).
Notice of Allowance in United States Patent Application No. 15/547,139, dated Aug. 7, 2019, 17 pages.
International Search Report in International Application No. PCT/JP2019/037690, dated Jan. 15, 2019, 7 pages.
Choi et al., "Molecular Targeted Therapy for Hepatocellular Carcinoma: Present Status and Future Directions," Biological and Pharmaceutical Bulletin, 2015, 38:986-991.
International Search Report in International Application No. PCT/JP2019/012971, dated May 14, 2019, 9 pages.
Notice of Allowance in Australian Patent Application No. 2015304465, dated Apr. 24, 2019, 3 pages.
Submission Document in Indonesian Patent Application No. P-00201505035, dated Apr. 26, 2019, 8 pages (with English Translation).
Tsuruoka et al., "Preclinical and clinical researches of lenvatinib mesylate (Lenvima capsule), a novel antitumor agent approved for thyroid cancer treatment," Folia Pharmacologica Japonica, 2015, 146:283-290 (with English Abstract).
Office Action in Israeli Patent Application No. 250290, dated Aug. 15, 2019, 8 pages (with English Translation).
Office Action in Korean Patent Application No. 10-2015-7022252, dated Sep. 5, 2019, 11 pages (with English Translation).
Office Action in Sri Lankan Patent Application No. 18355, dated Aug. 19, 2019, 1 page.
Submission Document in Mexican Patent Application No. MX/a/2017/001624, dated Aug. 21, 2019, 11 pages (with English Translation).
Notice of Allowance in U.S. Appl. No. 16/225,772, dated Oct. 22, 2019, 19 pages.
Submission Document in Chinese Patent Application No. 201680007472.7, dated Oct. 10, 2019, 16 pages (with English Translation).
Notice of Allowance in Korean Patent Application No. 10-2015-7022252, dated Nov. 11, 2019, 5 pages (with English Translation).
Notice of Allowance in Mexican Patent Application No. MX/a/2017/001624, dated Oct. 23, 2019, 5 pages (with English Translation).
Office Action in European Patent Application No. 15834302.0, dated Oct. 28, 2019, 4 pages.
Submission Document in Korean Patent Application No. 10-2015-7022252, dated Oct. 25, 2019, 43 pages (with English Translation).
Notice of Allowance in Pakistani Patent Application No. 94/2014, dated Dec. 31, 2019, 3 pages.
Notice of Allowance in Pakistani Patent Application No. 523/2016, dated Dec. 31, 2019, 3 pages.
Submission Document in Argentine Patent Application No. P140100495, dated Dec. 17, 2019, 7 pages (with English Translation).
Notice of Allowance in Chilean Patent Application No. 2015-02311, dated Dec. 12, 2019, 6 pages (with English Translation).
Notice of Allowance in U.S. Appl. No. 16/225,772, dated Dec. 16, 2019, 9 pages.
Notice of Allowance in U.S. Appl. No. 15/547,139, dated Dec. 5, 2019, 20 pages.
Office Action in Argentine Patent Application No. P140100495, dated Nov. 11, 2019, 4 pages (with English Translation).
Office Action in Israeli Patent Application No. 253701, dated Nov. 28, 2019, 7 pages (with English Translation).
Submission Document in Israeli Patent Application No. 250290, dated Nov. 28, 2019, 8 pages (with English Translation).
Submission Document in Israeli Patent Application No. 258671, dated Nov. 26, 2019, 4 pages (with English Translation).
Submission Document in Russian Patent Application No. 2017127135, dated Nov. 14, 2019, 21 pages (with English Translation).
Submission Document in Sri Lankan Patent Application No. 18355, dated Nov. 21, 2019, 3 pages.

(56) References Cited

OTHER PUBLICATIONS

Wu et al., "Identification of Targetable FGFR Gene Fusions in Diverse Cancers," Cancer Discovery, 2013 American Association for Cancer, Research Brief, 2013, 13 pages.
Office Action in Chinese Patent Application No. 201680007472.7, dated Jan. 15, 2020, 8 pages (with English Translation).
Notice of Allowance in Russian Patent Application No. 2017127135, dated Dec. 17, 2019, 16 pages (with English Translation).
Notice of Allowance in U.S. Appl. No. 16/225,772, dated Jan. 15, 2020, 9 pages.
Notice of Allowance in U.S. Appl. No. 15/547,139, dated Dec. 31, 2019, 13 pages.
Submission Document in Indian Patent Application No. 201747003469, dated Jan. 13, 2020, 12 pages.
Submission Document in Brazilian Patent Application No. BR112015019790-6, dated Dec. 30, 2019, 16 pages (with English Translation).
Notice of Allowance in Indonesian Patent Application No. P-00201505035, dated Sep. 27, 2019, 4 pages (with English Translation).
Submission Document in U.S. Appl. No. 16/225,772, dated Sep. 30, 2019, 10 pages.
International Search Report and Written Opinion in International Application No. PCT/JP2019/012971, dated May 14, 2019, 11 pages (with Partial Translation).
Kim et al., "Regorafenib in advanced hepatocellular carcinoma (HCC): considerations for treatment," Cancer Chemotherapy and Pharmacology, 2017, 80:945-954.
Llovet et al., "Sorafenib in Advanced Hepatocellular Carcninoma," The New England Journal of Medicine, 2008, 359:378-390.
Tsuruoka et al., "Preclinical and clinical researches of lenvatinib mesylate (Lenvima capsule), a novel antitumor agent approved for thyroid cancer treatment," Folia Pharmacologica Japonica, 2015, 146:283-290 (with English Translation).
International Search Report in International Application No. PCT/JP2018/037690, dated Jan. 15, 2019, 7 pages.
Notice of Allowance in Israeli Patent Application No. 250290, dated Mar. 17, 2020, 10 pages (with English Translation).
Notice of Allowance in U.S. Appl. No. 15/547,139, dated Mar. 24, 2020, 23 pages.
Notice of Allowance in U.S. Appl. No. 16/225,772, dated Apr. 14, 2020, 22 pages.
Office Action in Brazilian Patent Application No. BR112015019790-6, dated Apr. 7, 2020, 14 pages (with English Translation).
Office Action in Chinese Patent Application No. 201680007472.7, dated May 6, 2020, 8 pages (with English Translation).
Office Action in Chinese Patent Application No. 201680068110.9, dated Mar. 20, 2020, 15 pages (with English Translation).
Office Action in Indian Patent Application No. 201747027065, dated Jan. 28, 2020, 6 pages (with English Translation).
Office Action in Indian Patent Application No. 201847015401, dated May 5, 2020, 7 pages (with English Translation).
Office Action in Russian Patent Application No. 2018119102, dated Feb. 4, 2020, 12 pages (with English Translation).
Official Notification in Brazilian Patent Application No. BR112015019790-6, dated Mar. 10, 2020, 4 pages (with English Translation).
Submission Document in Chinese Patent Application No. 201680007472.7, dated Mar. 19, 2020, 8 pages (with English Translation).
Submission Document in European Patent Application No. 15834302.0, dated Feb. 19, 2020, 74 pages.
Submission Document in Russian Patent Application No. 2018119102, dated Apr. 27, 2020, 14 pages (with English Translation).
Office Action in European Patent Application No. 16768810.0, dated Jun. 18, 2020, 5 pages.
Office Action in Indian Patent Application No. 201747027065, dated Jul. 8, 2020, 2 pages (with English Translation).
Office Action in Israeli Patent Application No. 258671, dated Jun. 25, 2020, 8 pages (with English Translation).
Submission Document in Indian Patent Application No. 201747027065, dated May 21, 2020, 23 pages.
Submission Document in U.S. Appl. No. 16/642,105, dated Jun. 8, 2020, 99 pages.
Office Action in Australian Patent Application No. 2016237222, dated Sep. 2, 2020, 6 pages.
Submission Document in Brazilian Patent Application No. BR1120170022680, dated Aug. 31, 2020, 21 pages (with English Translation).
Notice of Allowance in U.S. Appl. No. 16/225,772, dated Jul. 24, 2020, 10 pages.
Submission Document in Chinese Patent Application No. 201680068110.9, dated Jul. 8, 2020, 8 pages.
Submission Document in European Patent Application No. 18865416.4, dated Jul. 29, 2020, 11 pages.
Office Action in Peruvian Patent Application No. 001748-2015, dated Apr. 19, 2019, 19 pages (with English Translation).
Notice of Allowance in Brazilian Patent Application No. BR112015019790-6, dated Aug. 11, 2020, 2 pages (with English Translation).
Submission Document in Indian Patent Application No. 201747027065, dated Aug. 18, 2020, 6 pages.
Notice of Allowance in Russian Patent Application No. 2018119102, dated Jun. 26, 2020, 12 pages (with English Translation).
Notice of Allowance in U.S. Appl. No. 15/547,139, dated Jun. 23, 2020, 11 pages.
Office Action in Israeli Patent Application No. 250290, dated Jan. 29, 2020, 10 pages (with English Translation).
Official Notification in Brazilian Patent Application No. BR112015019790-6, dated Jan. 21, 2020, 2 pages (with English Translation).
Submission Document in Israeli Patent Application No. 253701, dated Feb. 5, 2020, 7 pages (with English Translation).
Office Action in Mexican Patent Application No. MX/a/2018/006329, dated Jul. 17, 2020, 6 pages (with English Translation).
Office Action in Mexican Patent Application No. MX/a/2017/009892, dated Jul. 14, 2020, 7 pages (with English Translation).
Forner et al., "Hepatocellular Carcinoma," The Lancet, Mar. 2012, 379:1245-1255.
International Preliminary Report on Patentability in International Application No. PCT/JP2019/012971, dated Oct. 8, 2020, 8 pages.
Notice of Allowance in European Patent Application No. 16875716.9, dated Oct. 28, 2020, 18 pages.
Notice of Allowance in Israeli Patent Application No. 253701, dated Nov. 11, 2020, 9 pages (with English Translation).
Notice of Allowance in Mexican Patent Application No. MX/a/2017/009892, dated Dec. 15, 2020, 6 pages (with English Translation).
Notice of Allowance in Singaporean Patent Application No. 11201706143S, dated Oct. 29, 2020, 4 pages.
Notice of Allowance in U.S. Appl. No. 16/970,683, dated Jan. 15, 2021, 9 pages.
Office Action in Chinese Patent Application No. 201680068110.9, dated Nov. 24, 2020, 9 pages (with English Translation).
Office Action in Israeli Patent Application No. 272887, dated Nov. 23, 2020, 5 pages (with English Translation).
Office Action in U.S. Appl. No. 16/970,683, dated Oct. 9, 2020, 29 pages.
Submission Document in Chinese Patent Application No. 201980013339.6, dated Oct. 23, 2020, 6 pages (with English Translation).
Submission Document in European Patent Application No. 16768810.0, dated Sep. 30, 2020, 5 pages.
Submission Document in Indian Patent Application No. 201847015401, dated Oct. 29, 2020, 20 pages.
Submission Document in Israeli Patent Application No. 258671, dated Sep. 30, 2020, 35 pages (with English Translation).
Submission Document in Mexican Patent Application No. MX/a/2018/006329, dated Oct. 8, 2020, 7 pages (with English Translation).
Submission Document in U.S. Appl. No. 16/225,772, dated Oct. 21, 2020, 5 pages.

(56) References Cited

OTHER PUBLICATIONS

Submission Document in U.S. Appl. No. 16/970,683, dated Dec. 23, 2020, 22 pages.
Office Action in Japanese Application No. P2017-556119, dated Sep. 8, 2020, 6 pages (with English Translation).
Notice of Allowance in European Patent Application No. 16768810.0, dated Mar. 16, 2021, 71 pages.
Notice of Allowance in Japanese Patent Application No. P2017-556119, dated Mar. 16, 2021, 6 pages (with English Translation).
Notice of Allowance in U.S. Appl. No. 15/547,139, dated Feb. 5, 2021, 23 pages.
Notice of Allowance in U.S. Appl. No. 16/225,772, dated Mar. 29, 2021, 22 pages.
Notice of Allowance in U.S. Appl. No. 16/970,683, dated Feb. 10, 2021, 5 pages.
Notice of Allowance in U.S. Appl. No. 16/970,683, dated Apr. 16, 2021, 11 pages.
Office Action in Argentine Patent Application No. P140100495, dated Jan. 22, 2021, 10 pages (with English Translation).
Office Action in Australian Patent Application No. 2016237222, dated Jan. 29, 2021, 4 pages.
Office Action in Brazilian Patent Application No. BR1120170163926, dated Dec. 8, 2020, 10 pages (with English Translation).
Office Action in Brazilian Patent Application No. BR1120180101036, dated Feb. 9, 2021, 9 pages (with English Translation).
Office Action in Indian Patent Application No. 201747003469, dated Jan. 8, 2021, 2 pages (with English Translation).
Office Action in Mexican Patent Application No. MX/a/2018/006329, dated Jan. 19, 2021, 8 pages (with English Translation).
Submission Document in Australian Patent Application No. 2016237222, dated Jan. 19, 2021, 20 pages.
Submission Document in Australian Patent Application No. 2016237222, dated Mar. 22, 2021, 10 pages.
Submission Document in Brazilian Patent Application No. BR1120170163926, dated Mar. 5, 2021, 19 pages (with English Translation).
Submission Document in Chinese Patent Application No. 201680068110.9, dated Mar. 1, 2021, 14 pages (with English Translation).
Submission Document in Indian Patent Application No. 201747003469, dated Feb. 9, 2021, 8 pages.
Submission Document in Israeli Patent Application No. 272887, dated Mar. 16, 2021, 7 pages (with English Translation).
Submission Document in Mexican Patent Application No. MX/a/2018/006329, dated Mar. 11, 2021, 9 pages (with English Translation).
Submission Document in U.S. Appl. No. 16/970,683, dated Apr. 9, 2021, 5 pages.
Submission Document in Canadian Patent Application No. 2956270, dated Jun. 22, 2021, 26 pages.
[No Author], "Guidance for Industry—Estimating the Maximum Safe Starting Dose in Initial Clinical Trials for Therapeutics in Adult Healthy Volunteers," U.S. Department of Health and Human Services, Food and Drug Administration, Center for Drug Evluation and Reseach, Pharmacology and Toxicology, Jul. 2005, 30 pages.
European Search Report in European Application No. 18865416.4, dated May 28, 2021, 9 pages.
Koyama et al., "Abstract B160: First-in-human phase 1 study of E7090, a novel selective inhibitor of FGFRs, in patients with advanced solid tumors," Abstract, AACR-NCI-EORTC International Conference: Molecular Targets and Cancer Therapeutics, Jan. 2018, [Retrieved on May 18, 2021], retrieved from: URL<https://mct.aacrjournals.org/content/17/1_Supplement/B160>, 4 pages.
Notice of Allowance in Australian Patent Application No. 2016237222, dated Apr. 16, 2021, 4 pages.
Notice of Allowance in Malaysian Patent Application No. PI2015702696, dated Jul. 9, 2020, 2 pages (with English Translation).
Notice of Allowance in U.S. Appl. No. 15/547,139, dated May 12, 2021, 12 pages.
Notice of Allowance in U.S. Appl. No. 16/225,772, dated Jul. 12, 2021, 14 pages.
Notice of Allowance in U.S. Appl. No. 16/225,772, dated Jul. 23, 2021, 10 pages.
Notice of Allowance in U.S. Appl. No. 16/970,683, dated Jul. 30, 2021, 12 pages.
Office Action in Australian Patent Application No. 2016374441, dated May 31, 2021, 4 pages.
Office Action in Canadian Patent Application No. 2956270, dated Apr. 22, 2021, 4 pages.
Office Action in European Patent Application No. 15834302.0, dated May 14, 2021, 4 pages.
Office Action in Indian Patent Application No. 201847015401, dated Jun. 29, 2021, 3 pages (with English Translation).
Office Action in Israeli Patent Application No. 258671, dated May 10, 2021, 18 pages (with English Translation).
Office Action in Israeli Patent Application No. 276935, dated Apr. 22, 2021, 5 pages (with English Translation).
Office Action in Mexican Patent Application No. MX/a/2018/006329, dated May 14, 2021, 5 pages (with English Translation).
Office Action in U.S. Appl. No. 16/642,105, dated Jun. 28, 2021, 65 pages.
Submission Document in Brazilian Patent Application No. BR1120180101036, dated Apr. 26, 2021, 20 pages (with English Translation).
Submission Document in Israeli Patent Application No. 258671, dated Aug. 3, 2021, 4 pages (with English Translation).
Submission Document in Israeli Patent Application No. 276935, dated Jul. 13, 2021, 4 pages (with English Translation).
Submission Document in U.S. Appl. No. 16/970,683, dated Jul. 14, 2021, 5 pages.
Office Action in Chinese Patent Application No. 201680007472.7, dated Aug. 9, 2021, 10 pages (with English Translation).
Office Action in Indian Patent Application No. 202047007881, dated Nov. 12, 2021, 5 pages (with English Translation).
Notice of Allowance in U.S. Appl. No. 16/970,683, dated Nov. 10, 2021, 6 pages.
Office Action in Russian Patent Application No. 2020108284, dated Oct. 27, 2021, 23 pages (with English Translation).
European Search Report in European Application No. 19777797.2, dated Nov. 15, 2021, 8 pages.
Futami et al., "ASP5878, a Novel Inhibitor of FGFR1, 2, 3, and 4, Inhibits the Growth of FGF19-Expressing Hepatocellular Carcinoma," Molecular Cancer Therapeutics, 2017, 16(1):68-75, XP055858063.
Yu et al., "A FGFR1 inhibitor patent review: progress since 2010," Expert Opinion on Therapeutic Patents, 2016, pp. 1-16, XP055339480.
Formisano et al., "Association of FGFR1 with ERα Maintains Ligand-Independent ER Transcription and Mediates Resistance to Estrogen Deprivation in ER+ Breast Cancer," Clinical Cancer Research, 2017, 23(20):6138-6150.
International Search Report and Written Opinion in International Application No. PCT/JP2021/028008, dated Aug. 31, 2021 21 pages (with English Translation).
Katoh, "Fibroblast growth factor receptors as treatment targets in clinical oncology," Nature Reviews, Clinical Oncology, 2019, 16(2):105-122.
Musolino et al., "Phase II, randomized, placebo-controlled study of dovitinib in combination with fulvestrant in postmenopausal patients with HR+, HER2—breast cancer that had progressed during or after prior endocrine therapy," Breast Cancer Research, 2017, 19:18.
Notice of Allowance in Australian Patent Application No. 2016374441, dated Oct. 8, 2021, 3 pages.
Notice of Allowance in European Patent Application No. 15834302.0, dated Oct. 21, 2021, 56 pages.
Notice of Allowance in U.S. Appl. No. 15/547,139, dated Oct. 4, 2021, 24 pages.
Notice of Allowance in U.S. Appl. No. 15/547,139, dated Oct. 20, 2021, 12 pages.
Notice of Allowance in U.S. Appl. No. 16/970,683, dated Nov. 3, 2021, 16 pages.
Office Action in Brazilian Patent Application No. BR1120170022680, dated Apr. 7, 2020, 9 pages (with English Translation).

(56) References Cited

OTHER PUBLICATIONS

Office Action in Canadian Patent Application No. 2956270, dated Sep. 28, 2021, 3 pages.
Office Action in Korean Patent Application No. 10-2017-7002791, dated Aug. 29, 2021, 7 pages (with English Translation).
Office Action in U.S. Appl. No. 16/642,105, dated Oct. 18, 2021, 19 pages.
Quintela-Fandino et al., "Nintedanib plus letrozole in early breast cancer: a phase 0/1 pharmacodynamic, pharmacokinetic, and safety clinical trial of combined FGFR1 and aromatase inhibition," Breast Cancer Research, 2019, 21:69.
Seckl et al., "Radical trial: A phase Ib/IIa study to assess the safety and efficacy of AZD4547 in combination with either anastrozole or letrozole in ER positive breast cancer patients progressing on these aromatase inhibitors (AIs)," Journal of Clinical Oncology, 2017, 35(15):Supplement 1, 4 pages.
Submission Document in Australian Patent Application No. 2016374441, dated Sep. 22, 2021, 9 pages.
Submission Document in Brazilian Patent Application No. BR1120200038490, dated Sep. 9, 2021, 51 pages (with English Translation).
Submission Document in Canadian Patent Application No. 2956270, dated Oct. 25, 2021, 7 pages.
Submission Document in European Patent Application No. 15834302.0, dated Sep. 14, 2021, 75 pages.
Submission Document in Indian Patent Application No. 201847015401, dated Aug. 11, 2021, 6 pages.
Submission Document in Korean Patent Application No. 10-2017-7002791, dated Oct. 8, 2021, 23 pages (with English Translation).
Submission Document in U.S. Appl. No. 16/642,105, dated Sep. 15, 2021, 7 pages.
Submission Document in U.S. Appl. No. 16/970,683, dated Oct. 28, 2021, 5 pages.
Notice of Allowance in European Patent Application No. 15834302.0, dated Dec. 22, 2021, 56 pages.
Notice of Allowance in Korean Patent Application No. 10-2017-7002791, dated Nov. 29, 2021, 3 pages (with English Translation).
Notice of Allowance in U.S. Appl. No. 16/225,772, dated Dec. 21, 2021, 38 pages.
Notice of Allowance in U.S. Appl. No. 16/225,772, dated Jan. 11, 2022, 9 pages.
Office Action in Chinese Patent Application No. 201680068110.9, dated Jan. 24, 2022, 10 pages (with English Translation).
Office Action in Russian Patent Application No. 2020127993, dated Dec. 27, 2021, 21 pages (with English Translation).
Official Notification in Indian Patent Application No. 201847015401, dated Dec. 13, 2021, 21 pages.
Stahl et al., "Handbook of Pharmaceutical Salts Properties, Selection, and Use," 1st ed., Cover Page with Table of Contents, John Wiley & Sons, 2002, 4 pages.
Submission Document in Canadian Patent Application No. 2956270, dated Jan. 13, 2022, 5 pages.
Submission Document in Egyptian Patent Application No. PCT1285/2015, dated Jan. 4, 2022, 17 pages (with English Translation).
Submission Document in European Patent Application No. 15834302.0, dated Dec. 3, 2021, 6 pages.
Submission Document in European Patent Application No. 18865416.4, dated Dec. 16, 2021, 13 pages.
Submission Document in U.S. Appl. No. 16/642,105, dated Jan. 5, 2022, 17 pages.
Office Action in Egyptian Patent Application No. PCT1285/2015, dated Oct. 5, 2021, 11 pages (with English Translation).
Notice of Allowance in Canadian Patent Application No. 2956270, dated Apr. 12, 2022, 1 page (with English Translation).
Notice of Allowance in Russian Patent Application No. 2020127993, dated May 4, 2022, 12 pages (with English Translation).
Notice of Allowance in U.S. Appl. No. 16/225,772, dated Apr. 7, 2022, 11 pages.
Notice of Allowance in U.S. Appl. No. 16/225,772, dated Apr. 20, 2022, 13 pages.
Office Action in Canadian Patent Application No. 2974937, dated May 2, 2022, 5 pages.
Office Action in Chinese Patent Application No. 201680068110.9, dated Jun. 1, 2022, 15 pages (with English Translation).
Office Action in Indian Patent Application No. 202047007881, dated Jun. 1, 2022, 3 pages (with English Translation).
Office Action in Israeli Patent Application No. 258671, dated Apr. 12, 2022, 12 pages (with English Translation).
Office Action in Mexican Patent Application No. MX/a/2020/002083, dated May 12, 2022, 9 pages (with English Translation).
Office Action in Mexican Patent Application No. MX/a/2020/008610, dated Apr. 12, 2022, 7 pages (with English Translation).
Office Action in Russian Patent Application No. 2020108284, dated May 17, 2022, 30 pages (with English Translation).
Official Notification in U.S. Appl. No. 16/970,683, dated May 10, 2022, 4 pages.
Submission Document in European Patent Application No. 19777797.2, dated May 2, 2022, 18 pages.
Submission Document in Indian Patent Application No. 202047007881, dated May 11, 2022, 13 pages.
Submission Document in Mexican Patent Application No. MX/a/2020/008610, dated Jun. 15, 2022, 7 pages (with English Translation).
Submission Document in Russian Patent Application No. 2020108284, dated Mar. 17, 2022, 16 pages (with English Translation).
Submission Document in Russian Patent Application No. 2020127993, dated Mar. 11, 2022, 9 pages (with English Translation).
Submission Document in Indian Patent Application No. 201847015401, dated Mar. 10, 2022, 16 pages.
Office Action in Indian Patent Application No. 202047036696, dated Feb. 24, 2022, 6 pages (with English Translation).
Office Action in Sri Lankan Patent Application No. 18355, dated Feb. 28, 2022, 1 page.
Submission Document in Chinese Patent Application No. 201680068110.9, dated Mar. 8, 2022, 40 pages (with English Translation).
Notice of Allowance in U.S. Appl. No. 15/547,139, dated Mar. 4, 2022, 25 pages.
Office Action in U.S. Appl. No. 16/642,105, dated Mar. 10, 2022, 25 pages.
Office Action in Chinese Patent Application No. 201680007472.7, dated Feb. 25, 2022, 14 pages (with English Translation).
Submission Document in U.S. Appl. No. 16/642,105, dated Jun. 7, 2022, 10 pages.
ClinicalTrials.gov [online], "History of Changes for Study: NCT02275910 Phase 1 Study of E7090 in Subjects With Solid Tumor," Versions A & B of Jun. 26, 2017, retrieved from: URL<https://clinicaltrials.gov/ct2/history/NCT02275910?A=5&B=5&C=merged#StudyPageTop>, 4 pages.
Li et al., "Research and Development Progress on the Relationship between Small Molecule Anti-Tumor FGFR Inhibitor and FGFR Protein," Acta Pharmaceutica Sinica, 2016, 51(11):1689-1697 (with English Translation).
Notice of Allowance in Mexican Patent Application No. MX/a/2020/008610, dated Jul. 15, 2022, 4 pages (with English Translation).
Notice of Allowance in U.S. Appl. No. 15/547,139, dated Jul. 25, 2022, 22 pages.
Notice of Allowance in U.S. Appl. No. 16/225,772, dated Sep. 8, 2022, 23 pages.
Notice of Allowance in U.S. Appl. No. 16/225,772, dated Sep. 21, 2022, 10 pages.
Office Action in Australian Patent Application No. 2018349961, dated Jul. 19, 2022, 1 page.
Office Action in Brazilian Patent Application No. BR1120200038490, dated Sep. 13, 2022, 11 pages (with English Translation).
Office Action in Chinese Patent Application No. 201880055615.0, dated Aug. 1, 2022, 21 pages (with English Translation).
Office Action in Egyptian Patent Application No. PCT1285/2015, dated Aug. 7, 2022, 10 pages (with English Translation).
Office Action in Indian Patent Application No. 201847015401, dated Aug. 4, 2022, 3 pages (with English Translation).

(56) References Cited

OTHER PUBLICATIONS

Office Action in Israeli Patent Application No. 272887, dated Aug. 17, 2022, 3 pages.
Office Action in Japanese Application No. P2020-512051, dated Sep. 13, 2022, 8 pages (with English Translation).
Office Action in Mexican Patent Application No. MX/a/2020/002083, dated Jul. 21, 2022, 11 pages (with English Translation).
Office Action in U.S. Appl. No. 16/642,105, dated Jul. 25, 2022, 17 pages.
Submission Document in Indian Patent Application No. 202047036696, dated Jul. 15, 2022, 11 pages.
Submission Document in Israeli Patent Application No. 258671, dated Jul. 25, 2022, 24 pages.
Submission Document in Mexican Patent Application No. MX/a/2020/002083, dated Jul. 11, 2022, 21 pages (with English Translation).
Submission Document in Russian Patent Application No. 2020108284, dated Aug. 10, 2022, 11 pages (with English Translation).
Submission Document in Mexican Patent Application No. MX/a/2020/002083, dated Sep. 22, 2022, 2 pages (with English Translation).
[No Author], "Progress on molecular mechanism of liver cancer in general surgery department of Ruijin Hospital, Shanghai Jiaotong University School Of Medicine," Journal of Shanghai Jiaotong University (Medical Science), 2016, 36(7):1022 (with English Translation).
Bøttcher et al., "Treatment of advanced HR+/HER2- breast cancer with new targeted agents in combination with endocrine therapy: a review of efficacy and tolerability based on available randomized trials on everolimus, ribociclib, palbociclib and abemaciclib," Acta Oncologica, 2019, 58(2):147-153.
Deeks et al., "Exemestane—A Review of its Use in Postmenopausal Women with Breast Cancer," Drugs, 2009, 69(7):889-918.
Formisano et al., "Aberrant FGFR signaling mediates resistance to CDK4/6 inhibitors in ER+ breast cancer," Nature Communications, 2019, 10:1373, 14 pages.
Howell et al., "Comparison of fulvestrant versus tamoxifen for the treatment of advanced breast cancer in postmenopausal women previously untreated with endocrine therapy: a multinational, double-blind, randomized trial," Journal of Clinical Oncology, 2004, 22(9):1605-1613.
International Search Report in International Application No. PCT/JP2021/015546, dated May 25, 2021, 4 pages (with English Translation).
International Search Report in International Application No. PCT/JP2021/028008, dated Aug. 31, 2021, 6 pages (with English Translation).
Miyano et al., "E7090, a novel selective inhibitor of fibroblast growth factor receptors, displays potent antitumor activity and prolongs survival in preclinical models," Molecular Cancer Therapeutics, 2016, 15(11):2630-2639.
Nayar et al., "Acquired HER2 mutations in ER+ metastatic breast cancer confer resistance to estrogen receptor-directed therapies," Nature Genetics, 2019, 51:207-216.
Notice of Allowance in Brazilian Patent Application No. BR112017 0163926, dated Jan. 3, 2023, 6 pages (with English Translation).
Notice of Allowance in Korean Patent Application No. 10-2018-7014626, dated Dec. 19, 2022, 6 pages (with English Translation).
Notice of Allowance in U.S. Appl. No. 15/547,139, dated Nov. 17, 2022, 14 pages.
Office Action in Argentine Patent Application No. P140100495, dated Sep. 6, 2022, 6 pages (with English Translation).
Office Action in Brazilian Patent Application No. BR1120170163926, dated Oct. 11, 2022, 5 pages (with English Translation).
Office Action in Canadian Patent Application No. 2974937, dated Dec. 6, 2022, 3 pages.
Office Action in Canadian Patent Application No. 3001969, dated Nov. 9, 2022, 4 pages.
Office Action in Chinese Patent Application No. 201980013339.6, dated Oct. 10, 2022, 16 pages (with English Translation).
Office Action in Indian Patent Application No. 202047036696, dated Jan. 11, 2023, 2 pages (with English Translation).
Office Action in Israeli Patent Application No. 258671, dated Jan. 19, 2023, 13 pages (with English Translation).
Office Action in Japanese Application No. P2020-510951, dated Jan. 4, 2023, 7 pages (with English Translation).
Office Action in Mexican Patent Application No. MX/a/2020/002083, dated Nov. 29, 2022, 11 pages (with English Translation).
Office Action in Russian Patent Application No. 2020108284, dated Oct. 12, 2022, 11 pages (with English Translation).
Official Notification in Australian Patent Application No. 2019241625, Jan. 4, 2023, 1 page.
Seki et al., "Efficacy and Safety of Palbociclib and Fulvestrant in Japanese Patients With ER+/HER2-Advanced/Metastatic Breast Cancer," In Vivo, 2019, 33:2037-2044.
Submission Document in Brazilian Patent Application No. BR1120170163926, dated Dec. 23, 2022, 18 pages (with English Translation).
Submission Document in Brazilian Patent Application No. BR1120200038490, dated Dec. 9, 2022, 37 pages (with English Translation).
Submission Document in Indian Patent Application No. 201847015401, dated Oct. 18, 2022, 3 pages.
Submission Document in Singaporean Patent Application No. 10201913213W, dated Dec. 1, 2022, 8 pages.
Submission Document in Sri Lankan Patent Application No. 18355, dated Nov. 14, 2022, 2 pages.
Submission Document in U.S. Appl. No. 16/642,105, dated Oct. 25, 2022, 17 pages.
Wang et al., "Downregulation of microRNA-214 and overexpression of FGFR-1 contribute to hepatocellular carcinoma metastasis," Biochemical and Biophysical Research Communications, 2013, 439(1):47-53.
Ye et al., "Expression and Significance of FGFR2 in Colon Cancer," China Modern Doctor, 2012, 50(5):1-3 (with English Translation).
Notice of Allowance in U.S. Appl. No. 16/225,772, dated Jan. 12, 2023, 27 pages.
Notice of Allowance in U.S. Appl. No. 16/225,772, dated Jan. 24, 2023, 7 pages.
Submission Document in Chinese Patent Application No. 201980013339.6, dated Feb. 3, 2023, 14 pages (with English Translation).
International Preliminary Report on Patentability in Patent Application No. PCT/JP2021/028008, dated Feb. 9, 2023, 6 pages.
Notice of Allowance in Brazilian Patent Application No. BR1120180101036, dated Apr. 11, 2023, 7 pages (with English translation).
Notice of Allowance in U.S. Appl. No. 15/547,139, dated Apr. 10, 2023, 23 pages.
Office Action in Chinese Patent Application No. 201980013339.6, dated Feb. 12, 2023, 9 pages (with English Translation).
Office Action in Israeli Patent Application No. 276935, dated Jan. 3, 2023, 4 pages (with English Translation).
Office Action in Japanese Application No. P2020-512051, dated Mar. 7, 2023, 2 pages (with English Translation).
Office Action in Korean Patent Application No. 10-2017-7021185, dated Feb. 10, 2023, 10 pages (with English Translation).
Office Action in U.S. Appl. No. 16/642,105, dated Feb. 17, 2023, 24 pages.
Official Notification in Australian Patent Application No. 2019241625, dated Apr. 13, 2023, 1 page.
Submission Document in Argentine Patent Application No. P140100495, dated Feb. 10, 2023, 8 pages (with English Translation).
Submission Document in Canadian Patent Application No. 2974937, dated Mar. 9, 2023, 8 pages.
Submission Document in Canadian Patent Application No. 3001969, dated Feb. 15, 2023, 7 pages.
Submission Document in Japanese Patent Application No. P2020-510951, dated Feb. 28, 2023, 15 pages (with English Translation).
Submission Document in Korean Patent Application No. 10-2017-7021185, dated Apr. 3, 2023, 18 pages (with English translation).

(56) References Cited

OTHER PUBLICATIONS

Notice of Allowance in Korean Patent Application No. 10-2017-7021185, dated Apr. 27, 2023, 7 pages (with English Translation).
Notice of Allowance in U.S. Appl. No. 16/225,772, dated May 17, 2023, 13 pages.
Chen et al., "Anti-PD-1/PD-L1 therapy of human cancer: past, present, and future," The Journal of Clinical Investigation, 2015, 125(9):3384-3391.
International Preliminary Report on Patentability in Patent Application No. PCT/JP2021/039490, dated May 11, 2023, 6 pages.
International Search Report in International Application No. PCT/JP2021/039490, dated Dec. 14, 2021, 4 pages (with English Translation).
Notice of Allowance in Canadian Patent Application No. 2974937, dated Jun. 2, 2023, 1 page (with English Translation).
Notice of Allowance in Canadian Patent Application No. 3001969, dated May 26, 2023, 1 page (with English Translation).
Notice of Allowance in U.S. Appl. No. 15/547,139, dated Aug. 23, 2023, 15 pages.
Notice of Allowance in U.S. Appl. No. 16/225,772, dated Jun. 14, 2023, 8 pages.
Notice of Allowance in U.S. Appl. No. 16/225,772, dated May 26, 2023, 9 pages.
Office Action in Australian Patent Application No. 2018349961, dated Aug. 15, 2023, 4 pages.
Office Action in Chinese Patent Application No. 202180028460.3 dated Jun. 12, 2023, 13 pages (English Translation).
Office Action in Egyptian Patent Application No. PCT1285/2015, dated Apr. 10, 2023, 8 pages (with English Translation).
Submission Document in Chinese Patent Application No. 202180028460.3, dated Sep. 25, 2023, 31 pages (with English Translation).
Zhou et al., "CDK4/6 inhibitor resistance in estrogen receptor positive breast cancer, a 2023 perspective," Frontiers in Cell and Developmental Biology, Mar. 22, 2023, 11:1-12.
Notice of Allowance in Jordanian Application No. 39/2014, dated Apr. 16, 2018, 2 pages (with English translation).
Notice of Allowance in U.S. Appl. No. 15/547,139, dated Oct. 23, 2023, 7 pages.
Notice of Allowance in U.S. Appl. No. 15/547,139, dated Oct. 4, 2023, 7 pages.
Office Action in Chinese Patent Application No. 202180028460.3, dated Oct. 13, 2023, 10 pages (with English Translation).
European Search Report in European Application No. 21787967.5, dated Feb. 16, 2024, 9 pages.
European Search Report in European Application No. 21850938.8, Mar. 6, 2024, 8 pages.
Mouron et al., "FGFRI amplification or overexpression and hormonal resistance in luminal breast cancer: rationale for a triple blockade of Er, CDK4/6, and FGFRI," Breast Cancer Research (Online Edition), Feb. 12, 2021, 23(1):1-16.
Notice of Allowance in U.S. Appl. No. 15/547,139, dated Feb. 28, 2024, 6 pages.
Notice of Allowance in U.S. Appl. No. 15/547,139, dated Feb. 6, 2024, 6 pages.
Notice of Allowance in U.S. Appl. No. 15/547,139, dated Jan. 19, 2024, 7 pages.
Notice of Allowance in U.S. Appl. No. 16/225,772, dated Dec. 6, 2023, 39 pages.
Office Action in Indian Patent Application No. 201847015401, dated Dec. 22, 2023, 3 pages.
Office Action in Indian Patent Application No. 201847015401, dated Mar. 8, 2024, 6 pages.
Submission Document in Chinese Patent Application No. 202180028460.3, dated Dec. 21, 2023, 6 pages (with English Translation).
International Preliminary Report on Patentability in International Application No. PCT/JP2022/032309, dated Mar. 14, 2024, 7 pages.
Office Action in Chinese Patent Application No. 202180028460.3, dated Jan. 10, 2024, 9 pages (with English Translation).
International Preliminary Report on Patentability in International Application No. PCT/JP2022/032310, dated Mar. 14, 2024, 7 pages.
[No Author Listed], " Process Chemistry It is," from Pharmaceutical Synthesis to Manufacturing, 2nd Edition, 2014, pp. 143-144, Maruzen Publication Inc., Co., 5 pages (with partial English Translation).
Imamura et al., "Regioselective cleavage Reaction of the Aromatic methylenedioxy Ring. V. Cleavage with Sodium Alkoxides-Alcohols, Potassium tert-Butoxide-Alcohols, Dimsyl Anion-Methyl Alcohol, Metallic Sodium-Alcohols, and Sodium Cyanide in Dipolar Aprotic Solvents, " Chemical & Pharmaceutical Bulletin, 1992, 40(7):1691-1696.
International Search Report in International Application No. PCT/JP2022/032309, dated Nov. 15, 2022, 5 pages.
International Search Report in International Patent Application No. PCT/JP2022/032310, dated Nov. 15, 2022, 5 pages.
Notice of Allowance in Japanese Patent Application No. P2023-504017, dated Jul. 11, 2023, 5 pages (with English Translation).
Notice of Allowance in Japanese Patent Application No. P2023-504019, dated Jul. 11, 2023, 5 pages (with English Translation).
Notice of Allowance in U.S. Appl. No. 15/547,139, dated Dec. 22, 2023, 6 pages.
Notice of Allowance in U.S. Appl. No. 15/547,139, dated May 28, 2024, 14 pages.
Notice of Allowance in U.S. Appl. No. 15/547,139, dated, Jun. 18, 2024, 8 pages.
Notice of Allowance in U.S. Appl. No. 16/225,772, dated Apr. 2, 2024, 15 pages.
Office Action in Japanese Patent Application No. P2023-504017, dated Apr. 11, 2023, 6 pages (with English Translation).
Office Action in Japanese Patent Application No. P2023-504019, dated Apr. 11, 2023, 10 pages (with English Translation).
Submission Document in European Patent Application No. 21787967.5, dated May 13, 2024, 15 pages.
Yin et al., "A General and Efficient 2-Amination of Pyridines and Quinolines," Journal of Organic Chemistry, 2007, 72(12):4554-4557.
Notice of Allowance in U.S. Appl. No. 16/225,772, dated Jun. 26, 2024, 14 pages.
Office Action in Chinese Patent Application No. 202180045666.7, dated Jul. 31, 2024, 23 pages (with English Translation).
Cheng et al., "An overview of the binding models of FGFR tyrosine kinases in complex with small molecule inhibitors," European Journal of Medicinal Chemistry, 2017, 126:476-490.
European Search Report in European Application No. 21886203.5, dated Sep. 4, 2024, 10 pages.
Kawano et al., "Antitumor Activity of Tasurgratinib as an Orally Available FGFR1-3 Inhibitor in Cholangiocarcinoma Models With FGFR2-fusion," Anticancer Research, 2024, 44:2393-2406.
Notice of Allowance in U.S. Appl. No. 16/225,772, dated Sep. 20, 2024, 21 pages.
Office Action in Korean Patent Application No. 10-2020-7024300, dated Jul. 15, 2024, 8 pages (with English Translation).
Office Action in Russian Patent Application No. 2022127618, dated Aug. 14, 2024, 37 pages (with English Translation).
Submission Document in European Patent Application No. 21850938.8, dated Sep. 23, 2024, 12 pages (Response to the Communication pursuant to Rule 70(2)).
Submission Document in European Patent Application No. 21850938.8, dated Sep. 23, 2024, 39 pages (Response to the Invitation to file a translation of a previous application pursuant to R.53(3) EPC, Translations of the priority documents (JP2020130935 and JP2020163258)).
Kharkevich, "Farmakologia [Pharmacology], " Moscow: GEOTAR-Media, 10th Edition, 2010, pp. 76-77 (with English Translation).
Komarov et al., "The use of Aromatase Inhibitors in Hormone Full Therapy of Patients with Breast Cancer," Federal State Budgetary Scientific Institution, N. N. Blokhin National Medical Research Center of Oncology, Ministry of Health of Russia, 2016, pp. 17-25 (with English Translation).
Notice of Allowance in Thai Patent Application No. 1501004679, dated Oct. 31, 2024, 2 pages (with English Translation).
Office Action in Russian Patent Application No. 2022134723, dated Nov. 2, 2024, 34 pages (with English Translation).

(56) References Cited

OTHER PUBLICATIONS

Polyanskikh et al., "Current Understanding of Selective Estrogen Receptor Modulators," Journal of Obstetrics and Women's Diseases, 2019, 68(6):99-106 (with English Translation).
Submission Document in Chinese Patent Application No. 202180045666.7, dated Nov. 19, 2024, 61 pages (with English Translation).
Submission Document in Russian Patent Application No. 2022127618, dated Oct. 10, 2024, 23 pages (with English Translation).
Submission Document in Russian Patent Application No. 2022134723, dated Jan. 6, 2025, 25 pages (with English Translation).
Submission Document in U.S. Appl. No. 16/225,772, dated Dec. 18, 2024, 2 pages.
Tentsova, "Spravochnik Farmatsevta [Pharmacist's Reference Manual]," Corresponding Member of the Academy of Medical Sciences of the USSR, Moscow "Medicine," Second edition, revised and expanded, 1981, pp. 150-151 (with English Translation).
[No Author Listed], "Clinical guidelines for the diagnosis and treatment of patients with breast cancer," Approved at the Meeting of the Board of the Association of Oncologists of Russia, Moscow, 2014, pp. 1-43, 86 pages (with Machine Translation).
Kharkevich, "Pharmacology," Moscow: GEOTAR-Media, 10th Edition, 2010, pp. 73-74 (with English Translation).
Kholodov et al., "Clinical Pharmacokinetics," Moscow, "Medicine," 1985, Chapter 3, pp. 83-98, 134-138, 160, and 378-380, 52 pages (with English Translation).
Meshcheryakov et al., "Fulvestrant—endocrine therapy with an extended spectrum of action," Modern Oncology, 2012, 3(14):37-40, 7 pages (with English Translation).
Notice of Allowance in U.S. Appl. No. 15/547,139, dated Mar. 18, 2025, 12 pages.
Notice of Allowance in U.S. Appl. No. 16/225,772, dated Feb. 14, 2025, 6 pages.
Office Action in Chinese Patent Application No. 202180045666.7, dated Apr. 1, 2025, 17 pages (with English Translation).
Office Action in Chinese Patent Application No. 202210570963.X, dated Feb. 20, 2025, 10 pages (with English Translation).
Office Action in Israeli Patent Application No. 310338, dated Nov. 25, 2024, 5 pages (with English translation).
Office Action in Japanese Patent Application No. 2022-515429, dated Jan. 14, 2025, 6 pages (with English translation).
Office Action in Russian Patent Application No. 2022127618, dated Apr. 3, 2025, 15 pages (with English Translation).
Office Action in Russian Patent Application No. 2022127618, dated Dec. 10, 2024, 16 pages (with English Translation).
Office Action in Russian Patent Application No. 2022134723, dated Feb. 27, 2025, 28 pages (with English Translation).
Office Action in Singaporean Patent Application No. 10201913213W, dated Jan. 14, 2025, 8 pages.
Sergeev et al., "Short Course in Molecular Pharmacology," Moscow, 1975, p. 10, 3 pages (with English Translation).
Submission Document in Chinese Patent Application No. 202210570963.X, dated Feb. 5, 2025, 9 pages (with English Translation).
Submission Document in European Patent Application No. 21886203.5, dated Feb. 21, 2025, 12 pages.
Submission Document in Israeli Patent Application No. 310338, dated Mar. 18, 2025, 5 pages (with English Translation).
Submission Document in Israeli Patent Application No. 310339, dated Mar. 20, 2025, 5 pages (with English Translation).
Submission Document in Russian Patent Application No. 2022127618, dated Feb. 4, 2025, 5 pages (with English Translation).
Submission Document in Singaporean Patent Application No. 10201913213W, dated Mar. 12, 2025, 6 pages.
Wesserling et al., "Will In Vitro Tests Replace Animal Models in Experimental Oncology?," Journal of Tissue Science and Engineering, 2011, 2(1):202e, pp. 1-4.
Zhulenko et al., "Pharmacology," Moscow: KolosS, 2008, pp. 34-35 (with English Translation).

* cited by examiner

THERAPEUTIC AGENT FOR BREAST CANCER

TECHNICAL FIELD

The present invention relates to a therapeutic agent for breast cancer, comprising a monocyclic pyridine derivative having an FGFR inhibitory action or a pharmacologically acceptable salt thereof. The present invention relates more specifically to a therapeutic agent for breast cancer, comprising 5-((2-(4-(1-(2-hydroxyethyl)piperidin-4-yl)benzamide)pyridine-4-yl)oxy)-6-(2-methoxyethoxy)-N-methyl-1H-indole-1-carboxamide or a pharmacologically acceptable salt thereof.

BACKGROUND ART

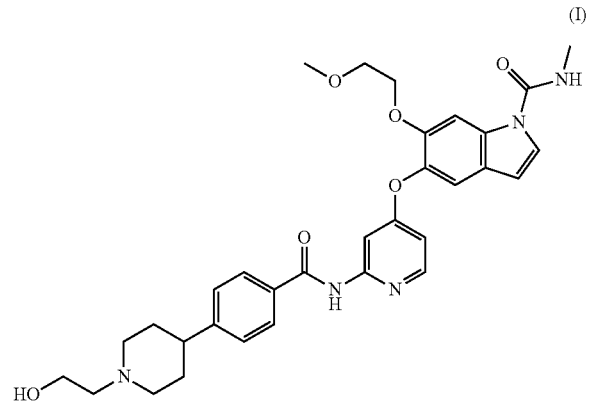 [SMILES: CNC(=O)n1ccc2cc(Oc3ccnc(NC(=O)c4ccc(C5CCN(CCO)CC5)cc4)c3)c(OCCOC)cc21]

5-((2-(4-(1-(2-hydroxyethyl)piperidin-4-yl)benzamide)pyridin-4-yl)oxy)-6-(2-methoxyethoxy)-N-methyl-1H-indole-1-carboxamide represented by formula (I) has been known as an inhibitor against fibroblast growth factor receptors (FGFR) 1, 2, and 3, and a report (Patent Literature 1) shows that this compound exerts a gastric cancer, lung cancer, bladder cancer, and endometrial cancer cell proliferation inhibitory action.

Breast cancer is grouped according to the presence or absence of expression of an estrogen receptor, a progesterone receptor, and a HER2 receptor. Drug therapy corresponding to each type can be provided as well as a surgical removal of an affected site. Unfortunately, even such therapeutic intervention results in a decrease in 5-year survival rate depending on the stage of breast cancer. In the case of breast cancer called a triple negative type where any of the above receptors are not expressed, in particular, administration of an anti-cancer drug such as taxane often exerts an insufficient effect (Non Patent Literature 1). Meanwhile, an FGFR inhibitor is reportedly effective in breast cancer treatment (Non Patent Literature 2).

CITATION LIST

Patent Literature

Patent Literature 1: U.S. Patent Application Publication No. 2014-235614

Non Patent Literature

Non Patent Literature 1: Foulkes et al., "Triple-Negative Breast Cancer", The New England Journal of Medicine, 363, 1938-1948, 2010.

Non Patent Literature 2: Koziczak et al., "Blocking of EGFR signaling inhibits breast cancer cell proliferation through downregulation of D-type cyclines", Oncogene, 23, 3501-3508, 2004.

SUMMARY OF INVENTION

Technical Problem

It is an objective of the present invention to provide a novel therapeutic agent for breast cancer.

Solution to Problem

In view of such situations, the present inventors have conducted intensive research and, as a result, have found that a compound represented by formula (I) elicits a marked anti-breast cancer therapeutic benefit. Then, the present invention has been completed.

Specifically, the present invention provides the following items [1] to [9].

[1] A therapeutic agent for breast cancer, comprising a compound represented by formula (I):

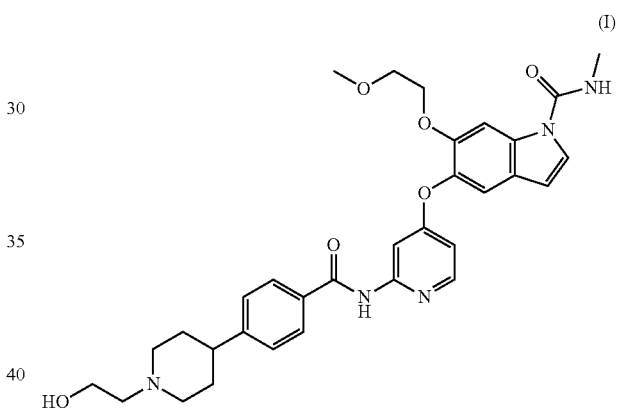

or a pharmacologically acceptable salt thereof.

[2] Use of a compound represented by formula (I) or a pharmacologically acceptable salt thereof for breast cancer treatment.

[3] A compound represented by formula (I) or a pharmacologically acceptable salt thereof for use in the treatment of breast cancer.

[4] A method of treating breast cancer comprising administering a compound represented by formula (I) or a pharmacologically acceptable salt thereof to a patient in need thereof.

[5] A composition for treating breast cancer comprising a compound represented by formula (I) or a pharmacologically acceptable salt thereof.

[6] A composition for treating breast cancer comprising a compound represented by formula (I) or a pharmacologically acceptable salt thereof and an excipient.

[7] The therapeutic agent, use, compound, method, or composition according to any one of the above items, wherein the breast cancer is locally advanced breast cancer, metastatic breast cancer, or recurrent breast cancer.

[8] The therapeutic agent, use, compound, method, or composition according to any one of the above items, wherein the breast cancer expresses an FGFR.

[9] The therapeutic agent, use, compound, method, or composition according to any one of the above items, wherein the FGFR is FGFR1, FGFR2, or FGFR3.

Advantageous Effects of Invention

The compound represented by formula (I) may exert an anti-breast cancer effect of reducing a tumor volume.

DESCRIPTION OF EMBODIMENTS

Figure 1:
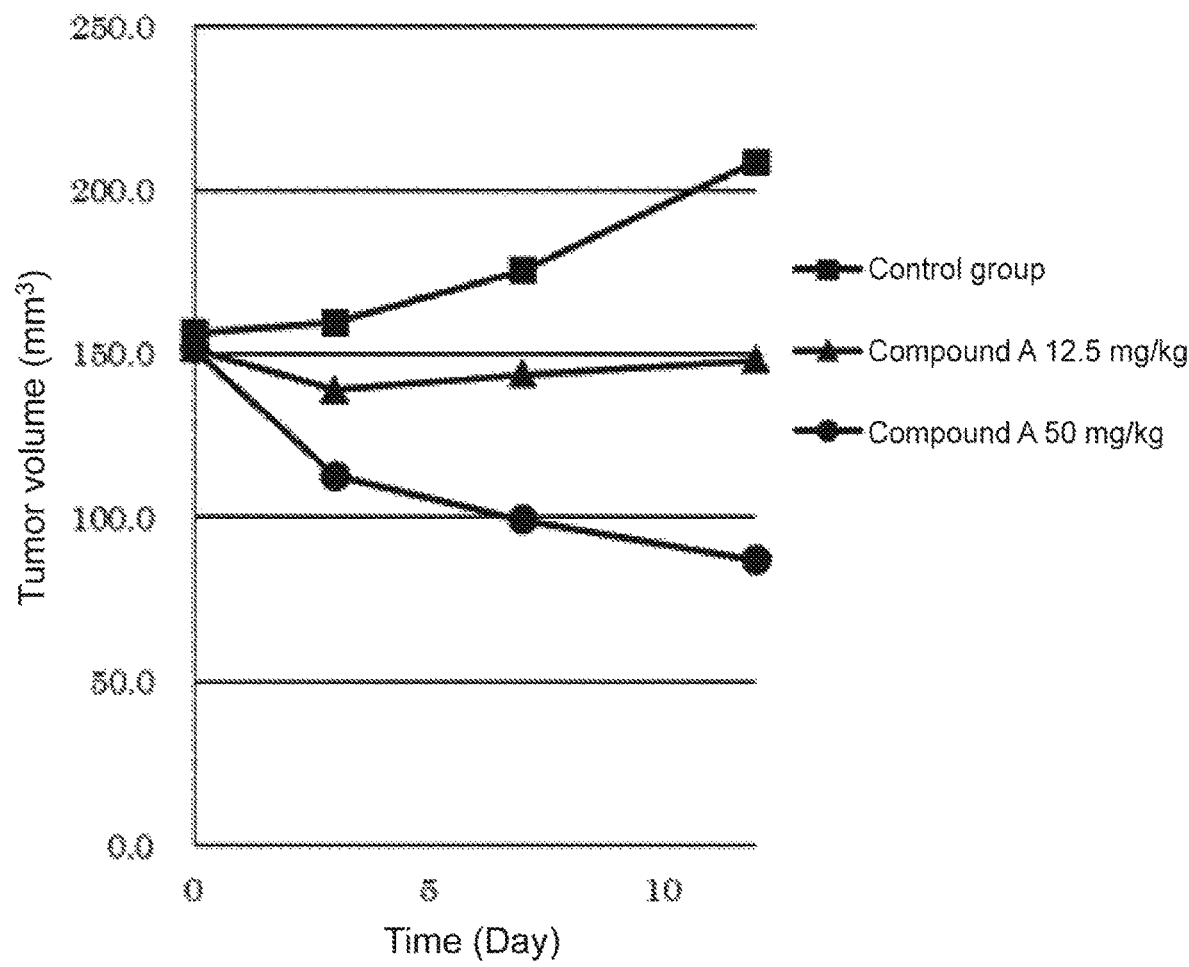
FIG. 1 is a graph showing changes in tumor volume over time after initiation of drug administration.

A compound represented by formula (I) or a pharmacologically acceptable salt thereof according to the present invention may be produced by the method described in Patent Literature 1.

As used herein, examples of the pharmacologically acceptable salt include a salt of an inorganic acid, a salt of an organic acid, and a salt of an acidic amino acid.

Preferable examples of the salt of the inorganic acid include salts of hydrochloric acid, hydrobromic acid, sulfuric acid, nitric acid, phosphoric acid, etc.

Preferable examples of the salt of the organic acid include salts of acetic acid, succinic acid, fumaric acid, maleic acid, tartaric acid, citric acid, lactic acid, stearic acid, benzoic acid, methanesulfonic acid, ethanesulfonic acid, p-toluenesulfonic acid, etc.

Preferable examples of the salt of acidic amino acid include salts of aspartic acid, glutamic acid, etc.

The preferable pharmacologically acceptable salt is a succinate or a maleate. The more preferable salt is a succinate. Particularly preferred is a 1.5 succinate.

The therapeutic agent for breast cancer according to the present invention may be orally administered in the form of a solid preparation, such as a tablet, granules, fine particles, powder, and a capsule, or a liquid, jelly, syrup, etc. Also, the therapeutic agent for tumor according to the present invention may be parenterally administered in the form of an injection, a suppository, ointment, a cataplasm, etc.

The therapeutic agent for breast cancer according to the present invention may be formulated by the protocol described in the Japanese pharmacopoeia, 16th edition.

The dose of a compound represented by formula (I) or a pharmacologically acceptable salt thereof may be suitably selected depending on the degree of a symptom, the age, sex, body weight, and a sensitivity difference of a patient, an administration route, dosing timing, a dosing interval, the kind of a pharmaceutical preparation, etc. When the compound is orally administered to an adult (the body weight: 60 kg), the daily dose is usually from 100 μg to 10 g, preferably from 500 μg to 10 g, and more preferably from 1 mg to 5 g. This dose may be administered while being divided into 1 to 3 times a day.

As used herein, the breast cancer means benign or malignant tumor developed in the mammary gland (breast ducts, lobules). The breast cancer includes locally advanced breast cancer, metastatic breast cancer, and recurrent breast cancer.

EXAMPLES

Hereinafter, the present invention is further described in detail by referring to Examples.

Production Example 1

Production of a salt of 5-((2-(4-(1-(2-hydroxyethyl)piperidin-4-yl)benzamide)pyridin-4-yl)oxy)-6-(2-methoxyethoxy)-N-methyl-1H-indole-1-carboxamide 1.5 succinate (Hereinafter, Sometimes Referred to as Compound A)

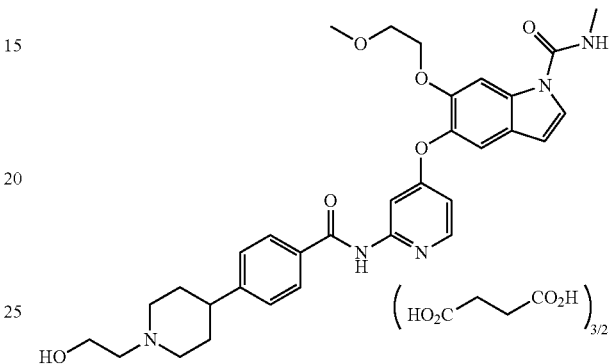

2.93 g of 5-({2-[({4-[1-(2-hydroxyethyl)piperidin-4-yl]phenyl}carbonyl)amino]pyridin-4-yl}oxy)-6-(2-methoxyethoxy)-N-methyl-1H-indole-1-carboxamide was weighed in a recovery flask, 60 mL of ethanol was added, and the mixture was heated and stirred at 70° C. in an oil bath to be dissolved. Succinic acid (1.23 g) was added, then turned off the oil bath and gradually cooled. The mixture was stirred at room temperature for 2 hours, and further stirred at 5° C. for 1 hour. The solid was collected by filtration to obtain the title compound (3.70 g).

$^1$H-NMR Spectrum (600 MHz, CD$_3$OD) δ (ppm): 1.96-2.10 (4H, m), 2.52 (6H, s), 2.93 (1H, m), 2.96 (3H, s), 3.01 (2H, m), 3.16 (2H, t, J=5.4 Hz), 3.22 (3H, s), 3.56 (2H, t, J=4.7 Hz), 3.61 (2H, m), 3.87 (2H, t, J=5.4 Hz), 4.14 (2H, t, J=4.6 Hz), 6.61 (1H, d, J=3.6 Hz), 6.68 (1H, dd, J=5.8, 2.3 Hz), 7.37 (1H, s), 7.42 (2H, d, J=8.3 Hz), 7.58 (1H, d, J=3.6 Hz), 7.73 (1H, d, J=2.2 Hz), 7.88 (2H, d, J=8.3 Hz), 8.08 (1H, s), 8.15 (1H, d, J=5.8 Hz).
$^{13}$C-NMR Spectrum (100 MHz, solid state) δ(ppm): 27.1, 28.3, 29.7, 34.8, 38.0, 41.3, 54.0, 57.3, 59.7, 60.9, 72.1, 72.5, 103.3, 104.2, 108.5, 116.9, 126.9, 128.6, 134.5, 136.7, 140.7, 149.4, 151.3, 155.1, 169.5, 170.1, 175.6, 179.9, 183.7.

Example 1: Growth Inhibitory Action of Compound A on Human Breast Cancer Cell Line (MFM223)

Four nude mice (BALB/cAJcl-nu/nu, female, CLEA Japan, Inc.) per group were used to evaluate an anti-tumor effect when compound A was administered.

A human-derived breast cancer cell line MFM223 (ECACC) was subjected to preparatory conditioning. The MFM223 cells were suspended at a concentration of 2×10$^8$ cells/mL in HBSS (Wako Pure Chemical Industries, Ltd.). To the resulting suspension was added an equal volume of Matrigel™ matrix (Becton, Dickinson and Company, Japan), and the mixture was mixed sufficiently. Then, 0.1 mL of the mixture was subcutaneously transplanted into the right flank of each nude mouse (CAnN.Cg-Foxn1nu/CrlCrlj, female, Charles River Laboratories International, Inc.). During rearing, β-estradiol (Wako Pure Chemical Industries, Ltd.) prepared at a final concentration of 2.5 µg/mL in drinking water was orally administered. 46 Days after the transplantation, a tumor formed was resected and cut into small pieces. HBSS containing Type I collagenase (SIGMA) at a final concentration of 380 units/mL and Deoxyribonuclease I (SIGMA) at a final concentration of 160 K units/mL was added thereto, and the mixture was stirred at 37° C. After the mixture was made to pass through a 100-µm cell strainer (Falcon®) and centrifuged to collect the cells, those cells were cultured in 10% bovine serum-containing EMEM culture medium.

The cells as so obtained were suspended at a concentration of $1.4 \times 10^8$ cells/mL in 10% bovine serum-containing EMEM culture medium (Wako Pure Chemical Industries, Ltd.). To the resulting suspension was added an equal volume of Matrigel™ matrix (Becton, Dickinson and Company, Japan), and the resulting mixture was mixed sufficiently. Next, 0.1 mL of the mixture was subcutaneously transplanted into the right flank of each mouse, and then, the anti-tumor effect was evaluated.

20 Days after the transplantation, an electronic digital caliper (Digimatic™ Caliper; Mitutoyo Corporation) was used to measure the long and short diameters of a tumor of interest. The mice were grouped such that each group had substantially the same average of the tumor volumes. Note that each tumor volume was calculated by using the following equation:

Tumor Volume (mm³)=Long Diameter (mm)×Short Diameter (mm)×Short Diameter (mm)/2.

Compound A as obtained in Production Example 1 was dissolved at a concentration of 0.625 mg/mL, or 2.5 mg/mL in purified water.

Then, the solution was orally administered at a dose of 20 mL/kg, i.e., 12.5 mg/kg or 50 mg/kg, once a day for 12 days to the mice of each group. Purified water was administered at 20 mL/kg to the control group.

Figure 2:
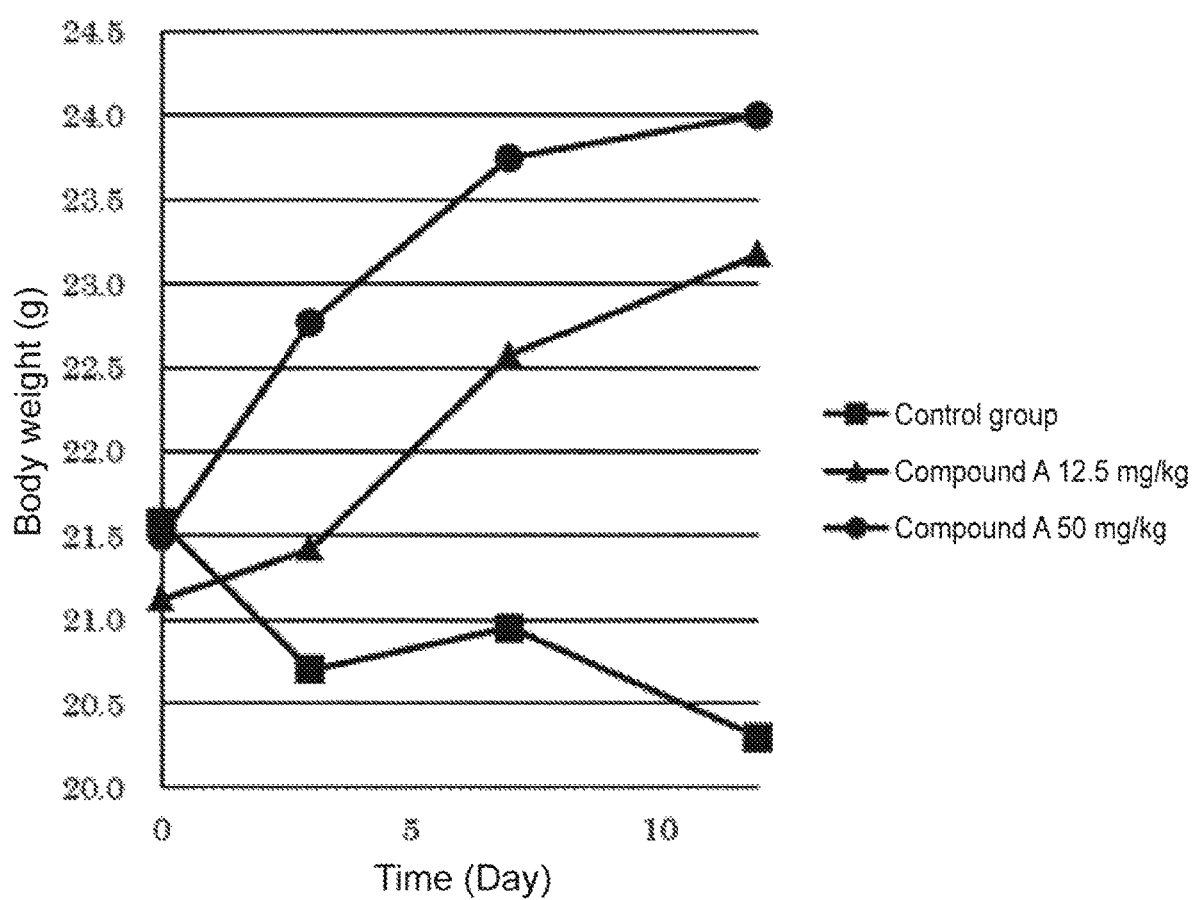
FIG. 2 is a graph showing changes in body weight over time after initiation of drug administration.

On day 3, 7, and 12 after initiation of the administration, the tumor volume of each mouse was measured. Table 1 and FIG. 1 show the results. In addition, Table 2 and FIG. 2 show changes in body weight over time.

TABLE 1

Changes in tumor volume over time (mm³)

|  |  | Day 0 | Day 3 | Day 7 | Day 12 |
|---|---|---|---|---|---|
| Control group |  | 156.6 | 159.7 | 175.5 | 208.4 |
| Compound A | 12.5 mg/kg | 151.6 | 139.0 | 143.8 | 148.2 |
| Compound A | 50 mg/kg | 151.6 | 112.8 | 99.3 | 87.2 |

TABLE 2

Changes in body weight over time (g)

|  |  | Day 0 | Day 3 | Day 7 | Day 12 |
|---|---|---|---|---|---|
| Control group |  | 21.6 | 20.7 | 21.0 | 20.3 |
| Compound A | 12.5 mg/kg | 21.1 | 21.4 | 22.6 | 23.2 |
| Compound A | 50 mg/kg | 21.5 | 22.8 | 23.8 | 24.0 |

The invention claimed is:

1. A method of treating breast cancer comprising administering 5-((2-(4-(1-(2-hydroxyethyl)piperidin-4-yl)benzamide)pyridin-4-yl)oxy)-6-(2-methoxyethoxy)-N-methyl-1H-indole-1-carboxamide or a pharmacologically acceptable salt thereof to a patient in need thereof.

2. The method according to claim 1, wherein the salt is a 1.5 succinate.

3. The method according to claim 1, wherein the breast cancer is locally advanced breast cancer, metastatic breast cancer, or recurrent breast cancer.

4. The method according to claim 2, wherein the breast cancer is locally advanced breast cancer, metastatic breast cancer, or recurrent breast cancer.

* * * * *